United States Patent
Gordon et al.

(10) Patent No.: US 6,969,539 B2
(45) Date of Patent: Nov. 29, 2005

(54) VAPOR DEPOSITION OF METAL OXIDES, SILICATES AND PHOSPHATES, AND SILICON DIOXIDE

(75) Inventors: Roy G. Gordon, Cambridge, MA (US); Jill Becker, Cambridge, MA (US); Dennis Hausmann, Los Gatos, CA (US); Seigi Suh, Pleasanton, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 10/381,628

(22) PCT Filed: Sep. 28, 2001

(86) PCT No.: PCT/US01/30507

§ 371 (c)(1),
(2), (4) Date: Sep. 2, 2003

(87) PCT Pub. No.: WO02/27063

PCT Pub. Date: Apr. 4, 2002

(65) Prior Publication Data

US 2004/0043149 A1 Mar. 4, 2004

Related U.S. Application Data

(60) Provisional application No. 60/236,283, filed on Sep. 28, 2000, and provisional application No. 60/253,917, filed on Nov. 29, 2000.

(51) Int. Cl.[7] .............................................. C23C 16/40
(52) U.S. Cl. .............................. 427/255.29; 427/255.38
(58) Field of Search ........................ 427/255.29, 255.38

(56) References Cited

U.S. PATENT DOCUMENTS

| | | | | |
|---|---|---|---|---|
| 4,386,117 A | * | 5/1983 | Gordon | 427/109 |
| 4,474,642 A | * | 10/1984 | Nakane et al. | 438/669 |

(Continued)

FOREIGN PATENT DOCUMENTS

| | | |
|---|---|---|
| DE | 43/16883 | 11/1994 |
| EP | 0560617 | 9/1993 |
| EP | 1067595 A2 | 1/2001 |
| EP | 1067595 A3 | 1/2002 |
| JP | 04359515 | 11/1992 |
| JP | 2002093803 A2 | 3/2002 |
| JP | 2002093804 A2 | 3/2002 |
| WO | 97/38355 | 10/1997 |
| WO | 98/15669 | 4/1998 |
| WO | 99/29924 | 6/1999 |
| WO | 99/29926 | 6/1999 |
| WO | WO-01/27347 | 4/2001 |
| WO | 01/45158 | 6/2001 |
| WO | 02/27063 | 4/2002 |

OTHER PUBLICATIONS

Lee, et al., "Mass Production Worthy $HfO_2$–$Al_2O_3$ Laminate Capacitor Technology using Hf Liquid Precursor for Sub–100nm DRAMs," Presented at IEEE IEDM (International Electronic Devices Meeting), San Francisco, CA, Dec. 9–11 (2002), pp 1–4.

(Continued)

*Primary Examiner*—Bret Chen
(74) *Attorney, Agent, or Firm*—Wilmer Cutler Pickering Hale and Dorr LLP

(57) ABSTRACT

Metal silicates or phosphates are deposited on a heated substrate by the reaction of vapors of alkoxysilanols or alkylphosphates along with reactive metal amides, alkyls or alkoxides. For example, vapors of tris-(ter-butoxy)silanol react with vapors of tetrakis(ethylmethylamido)hafnium to deposit hafnium silicate on surfaces heated to 300° C. The product film has a very uniform stoichiometry throughout the reactor. Similarly, vapors of diisopropylphosphate react with vapors of lithium bis(ethyldimethylsilyl)amide to deposit lithium phosphate films on substrates heated to 250° C. supplying the vapors in alternating pulse produces these same compositions with a very uniform distribution of thickness and excellent step coverage.

31 Claims, 3 Drawing Sheets

U.S. PATENT DOCUMENTS

| | | | |
|---|---|---|---|
| 4,723,978 A | * 2/1988 | Clodgo et al. | 216/55 |
| 4,792,463 A | 12/1988 | Okada et al. | |
| 5,389,401 A | 2/1995 | Gordon | |
| 5,403,630 A | 4/1995 | Matsui et al. | |
| 5,710,075 A | 1/1998 | Tseng | |
| 5,922,787 A | * 7/1999 | Kondo et al. | 523/122 |
| 6,090,442 A | 7/2000 | Klaus et al. | |
| 6,335,288 B1 | 1/2002 | Kwan et al. | |
| 6,339,004 B1 | 1/2002 | Kim | |
| 6,342,432 B1 | 1/2002 | Wang | |
| 6,395,209 B2 | * 5/2002 | Yoshida et al. | 264/137 |
| 6,534,395 B2 | 3/2003 | Werkhoven et al. | |
| 6,867,152 B1 | 3/2005 | Hausmann et al. | |
| 2002/0004281 A1 | 1/2002 | Lee et al. | |
| 2002/0018849 A1 | 2/2002 | George et al. | |
| 2002/0102814 A1 | 8/2002 | Olsen | |
| 2003/0015764 A1 | 1/2003 | Raaijmakers et al. | |
| 2004/0018694 A1 | 1/2004 | Lee et al. | |

OTHER PUBLICATIONS

Park, et al., "Mass–Productive Ultra–Low Temperature ALD $SiO_2$ Process Promising for Sub–90nm Memory and Logic Devices," Presented at IEEE IEDM (International Electron Devices Meeting), San Francisco, CA, Dec. 9–11 (2002), pp 1–4.

Coltrin, et al., "Chemical kinetics in chemical vapor deposition: growth of silicon dioxide from tetraethoxysilane (TEOS)," *Thin Solid Films*, vol. 365, pp. 251–263 (2000).

Ikeda, et al., "Ozone/Organic–Source APCVD for USLI Reflow Glass Films," *NEC Research & Development*, No. 94, pp. 1–7 (1989).

Hausmann, et al., "Rapid Vapor Deposition of Highly Conformal Silica Nanolaminates," *Science*, vol. 298, pp. 402–406 (2002).

Kingon, et al., "Alternative dielectrics to silicon dioxide for memory and logic devices," *Nature*, vol. 406, pp. 1032–1038, (2000).

Ritala, "Advanced ALE processes of amorphous and polycrystalline films," *Applied Surface Science*, vol. 112, pp. 223–230, (1997).

Ritala, et al., "Atomic Layer Deposition of Oxide Thin Films with Metal Alkoxides as Oxygen Sources," *Science*, vol. 288, pp. 319–321, (2000).

Backer, et al., "Esters Mixtes De L'Acide Tetrathio Orthosilicique," *Rec. Trav. Chim.*, vol. 61, pp. 500–512, (1942).

Okamoto, et al., "Convenient Synthetic Route To Mono–Or Dialkyl Phosphate From Inorganic Phosphorus Acids," *Phosphorus, Sulfur and Silicon*, vol. 55, pp. 195–200 (1991).

McIvor, et al., "Preparation and Toxicity of Some Alkyl Thiopyrophosphates," *Canadian J. Chemistry*, vol. 34, pp. 1825–1827 (1956).

Zwierzak, et al., "Organophosphorus Esters—tButyl As Protecting Group In Phosphorylation Via Nucleophilic Displacement," *Tetrahedron*, vol. 27, pp. 3163–3170 (1971).

George, et al., "Atomic Layer Controlled Depositon of $SiO2$ and $Al2O3$ Using ABAB . . . binary reaction sequence chemistry," *Appl. Surf. Sci.*, 82/83, pp. 460–467 (1994).

Gasser, et al., "Qusai–Monolayer Deposition of Silicon Dioxide," *Thin Solid Films*, vol. 250, pp. 213–218 (1994).

Klaus, et al., "Atomic Layer Deposition of $SiO2$ at Room Temperature Using $NH3$–catalyzed Sequential Surface Reactions," *Surf. Sci.*, vol. 447, pp. 81–90 (2000).

Ferguson, et al., "Atomic Layer Deposition of $Al2O3$ and $SIO2$ on BN Particles Using Sequential Surface Reactions," *Applied Surface Science*, vols. 162–163, pp. 280–292, (2000).

Yamaguchi, et al., "Atomic Layer Chemical–Vapor–Deposition of Silicon Dioxide Films with an Extremely Low Hydrogen Content," *Applied Surface Science*, vols. 130–132, pp. 202–207 (1998).

Morishita, et al., "New Substances for Atomic–Layer Deposition of Silicon Dioxide," *J. Non–Crystalline Solids*, vol. 187, pp. 66–69 (1995).

Klaus, et al., "Atomic Layer Deposition of $SiO2$ Using Catalyzed and Uncatalyzed Self–Limiting Surface Reactions," *Surface Review and Letters*, vol. 6(3), pp. 435–448 (1999).

Ferguson, et al., "Atomic Layer Deposition of $SiO2$ Fims on BN Particles Using Sequential Surface Reactions," *Chem. Mater*, vol. 12, pp. 3472–3480 (2000).

* cited by examiner

VAPOR DEPOSITION OF METAL OXIDES, SILICATES AND PHOSPHATES, AND SILICON DIOXIDE

RELATED APPLICATIONS

This application claims priority under 37 CFR §1.119 (e) from copending application Ser. Nos. 60/236,283, filed Sep. 28, 2000 entitled "Vapor Deposition of Metal Silicates and Phosphates" and 60/253,917, filed Nov. 29, 2000, entitled "Vapor Deposition of Metal Oxides, Silicates and Phosphates, and Silicon Dioxide".

STATEMENT AS TO FEDERALLY SPONSORED RESEARCH

This invention was made with the support of the United States government under National Science Foundation Grant No. ECS-9975504. The United States may have certain rights in the invention.

BACKGROUND OF THE INVENTION

1. Field of the Invention

This invention relates to novel reagents for use in thin film deposition processes such as chemical vapor deposition (CVD) and atomic layer deposition (ALD). These reagents can be used for deposition of materials containing silicon and/or phosphorus along with metals and/or oxygen, commonly called metal oxides, silicates or metal phosphates, or silicon dioxide.

2. Description of the Related Art

Chemical vapor deposition (CVD) is a widely-used process for forming solid materials, such as coatings or powders, from reactants in the vapor phase. Comprehensive reviews of CVD processes have been given recently in *CVD of Nonmetals*, W. S. Rees, Jr., Editor, VCH Publishers, Weinheim, Germany, 1996; *CVD of Compound Semiconductors*, A. C. Jones and P. O'Brien, VCH, 1996; and *The Chemistry of Metal CVD*, T. Kodas and M. Hampden-Smith, Editors, VCH, 1994.

In CVD processes, a reactant vapor or vapor mixture is brought into contact with a heated surface on which a thin film is deposited. In a related form of CVD, two reactant vapors are alternately exposed to the heated surface. This form of CVD is often called atomic layer deposition (ALD). For suitable reactants, ALD can provide improved step coverage and thickness uniformity compared to CVD with mixed vapors. For a review of ALD, see the paper by Mikko Ritala in *Applied Surface Science*, volume 112, pages 223–230 (1997).

Coatings of metal silicates have many applications or potential applications. For example, silicates of zirconium, hafnium, yttrium or lanthanum are being considered as potential replacements for silicon dioxide in gate insulators in silicon semiconductor technology. See, for example, A. Kingon et al., *Nature*, volume 406, pages 1032–1038 (2000). In *Science*, (volume 288, pages 319 to 321 (2000)), Ritala et al. report the use of the sequential ALD reaction of metal chlorides and silicon alkoxides to produce metal silicates, including zirconium silicate. However, this reaction deposits films containing residual chlorine, which can be deleterious to the properties of the film or to its adhesion to substrates or subsequent coatings. The chlorine in the precursors can also corrode metal substrates or the apparatus used for the deposition. Thus it would be advantageous to have chlorine-free precursors for CVD or ALD of metal silicates or oxides.

ALD of silicon dioxide has been achieved by Klaus et al., U.S. Pat. No. 6,090,442 (2000), but the deposition rate is very slow and the substrate temperature is limited to values near room temperature.

Lithium phosphate is a material of current interest as a lithium ion conductor in lithium batteries. Currently there is no known process for CVD or ALD of lithium phosphate.

SUMMARY OF THE INVENTION

A principal feature of the present invention includes volatile chemical precursors with reactivity adapted for CVD or ALD of metal silicates, phosphates or oxides.

An advantage of these chemical precursors is that they do not contain chlorine, and leave no chlorine residue during a process for the CVD or ALD of metal silicates, phosphates or oxides.

A related feature of the present invention is the deposition of metal silicates under conditions that produce a sharp interface between silicon substrates and the deposited metal silicate.

An advantage of the process is that it permits deposition of materials containing metal silicates or phosphates by a CVD process in which all the reactants may be mixed homogeneously before delivery to the heated surface of the substrate.

An additional advantage of the process is the vapor deposition of metal silicates or phosphates with relatively fixed ratio of metal to silicon over a range of conditions such as concentrations of reactants and position of the substrate inside the reactor.

Another advantage of the invention is its ability to make conformal coatings over substrates with narrow holes, trenches or other structures. This ability is commonly known as good step coverage.

Another feature of the present invention is the preparation of material comprising lithium phosphate.

An advantage of the invention is that the reactants are stable and relatively nonhazardous.

Another feature of the invention includes a chemical vapor deposition or atomic layer deposition process for metal oxides or mixtures of metal oxides.

A further feature of the invention includes process for atomic layer deposition of silicon dioxide.

One particular feature of the present invention includes a process for depositing oxides or silicates of zirconium, hafnium, yttrium and/or lanthanum having high dielectric constants of use as gate insulators or trench capacitors in microelectronic devices.

Another particular feature of the present invention includes a process for depositing silicon dioxide or metal silicates having useful optical properties, such as in planar waveguides and multiplexers/demultiplexers, and in optical interference filters.

An additional feature of the present invention includes a process for depositing lithium phosphate coatings allowing rapid diffusion of lithium for use as separators in batteries or electrochromic devices.

Other features and advantages of the invention will be obvious to those skilled in the art on reading the instant invention.

In one aspect of the invention vapors of alkoxysilanols are reacted with the vapors of suitably reactive metal or metalloid compounds, such as metal or metalloid alkylamides, alkyls or cyclopentadienyls, to form metal silicates. The reaction may be carried out in a manner to form films.

In at least some embodiments, tris(alkoxy)silanol compounds have the general formula 1, in which R″ represents hydrogen, alkyl groups, fluoroalkyl groups or alkyl groups substituted with other atoms or groups, preferably selected to enhance the volatility of the compound, where R″ is any one of $R^1$ through $R^n$. The $R^n$ may be the same or different from each other.

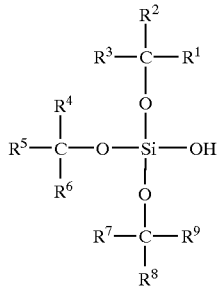

1

In at least some embodiments methyl groups are selected for each of the R″ in the general formula 1 given above one obtains a highly preferred compound tris(tert-butoxy)silanol 2, which may be written more compactly as $(^tBuO)_3SiOH$.

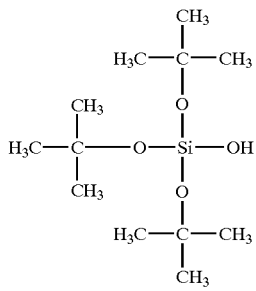

2

Another compound of the invention is tris(tert-pentyloxy) silanol, also known as tris(tert-amyloxy)silanol 3, which may be written more compactly as $(^tAmO)_3SiOH$.

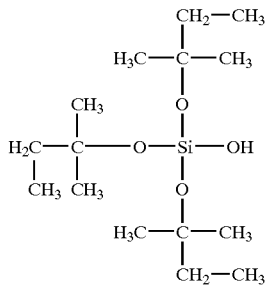

3

In at least some embodiments of the invention Di(alkoxy) silanediols such as $(^tBuO)_2Si(OH)_2$ can also be used, although they are less stable than tris(alkoxy)silanol compounds in at least some applications. Di(alkoxy)silanediol compounds having the general formula 4 may be used according to the invention, where R″, represents hydrogen, alkyl groups, fluoroalkyl groups or alkyl groups substituted by other atoms or groups, preferably selected to enhance volatility and stability, and may be the same or different for any R″, and R″ is any of $R^1$ through $R^6$ may be the same or different.

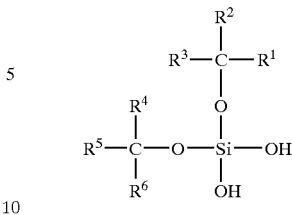

4

In at least some embodiments, the groups $R^1$ for the general formula 1 or $R^1$–$R^6$ for the general formula 4 may be selected from the group consisting of hydrogen, methyl, ethyl, n-propyl and isopropyl groups.

In the foregoing compounds, it is also understood that the alkyl groups $R^1$ through $R^9$ for general formula or $R^1$ through $R^6$ for general formula 4 may be a hydrocarbon having some degrees of unsaturation, e.g., aryl, alkenyl or alkynyl groups.

In at least some embodiments, metal compounds include those that react readily with the slightly acidic protons in silanols. These acidic protons are the ones attached directly to oxygen in the silanol. Metal compounds that generally react with these acidic protons include most metal alkyls and other organometallic compounds, metal alkylamides, and some metal alkoxides. The reactivity of any particular compound can be established readily by mixing it with an alkoxysilanol and analyzing the mixture for products by techniques such as nuclear magnetic resonance (NMR). We have found that compounds that are known to react with water also generally react with alkoxysilanols.

We have also discovered that the stoichiometry of the deposited metal silicates can be controlled. The silicon/metal ratio may be decreased by replacing some or all of the silanol with water or an alcohol. Conversely, the silicon/metal ratio may be increased by replacing some or all of the metal source by a suitably reactive silicon-containing compound such as a silicon amide or a silylene. By these methods the composition of the deposited material may be chosen to be any composition from pure metal oxide to pure silicon dioxide or any desired silicon/metal ratio in between. The stoichiometry may even be varied during the course of one deposition. For example, in the deposition of a gate insulator for a silicon semiconductor device, it may be desirable to begin the deposition with a silicon-rich layer close to the silicon surface in order to improve the electrical properties of the interface, followed by a metal-rich layer with higher dielectric constant.

In another aspect of the invention, vapors of bis(alkyl) phosphates are reacted with the vapors of reactive metal compounds, such as metal alkylamides, metal alkyls, metal cyclopentadienides or metal alkoxides, to form metal phosphates. The reaction may be carried out in a way that forms films.

In at least some embodiments of the invention, phosphorus-containing precursors include bis(alkyl) phosphates 5 in which R″, represents hydrogen, alkyl groups, fluoroalkyl groups or alkyl groups, substituted with other atoms or groups where R″ may be any of $R^1$ through $R^6$. The R″ may be the same or different from each other.

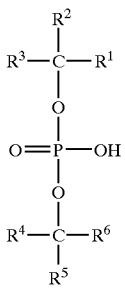

In at least one embodiment, the phosphorus precursor is diisopropylphosphate, represented by the formula 6.

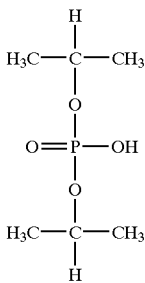

It is also possible to control the stoichiometry of the metal phosphates. The phosphorus/metal ratio may be decreased by replacing some or all of the bis(alkyl)phosphate with water or an alcohol. Conversely, the phosphorus/metal ratio may be increased by replacing some or all of the metal source by a suitably reactive phosphorus source. By these methods, the composition of the deposited material may be varied from pure metal oxide to pure phosphorus oxide or any desired phosphorus/metal ratio.

In at least some embodiments, the groups $R^1$–$R^6$ for the general formula 5 may be selected from the group consisting of hydrogen, methyl, ethyl, n-propyl or isopropyl groups. In the foregoing compounds, it is also understood that the alkyl groups $R^1$ through $R^9$ for general formula 1 or $R^1$ through $R^6$ for general formula 4 may be a hydrocarbon having some degrees of unsaturation, e.g., aryl, alkenyl or alkynyl groups.

In another aspect of the invention, a process for preparing a material comprising silicon includes exposing a substrate to one or more vapors chosen from the group consisting of alkoxysilanols, alkoxysilanediols and silylenes. In at least some embodiments, the silylene is the compound described by the formula

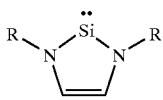

where R is an alkyl group, or R is tert-butyl.

In one aspect of the invention, a process for forming a material including phosphorus includes exposing a substrate to one or more vapors chosen from the group consisting of bis(alkyl)phosphates, phosphorus(III) oxide and white phosphorus.

In another aspect of the invention, a process is provided for preparing oxygen-containing materials including exposing a substrate to one or more vapors chosen from the group consisting of arene hydrates, such as benzene hydrate, naphthalene hydrate, or a substituted benzene hydrate or a substituted naphthalene hydrate.

In another aspect of the invention, a process for forming a metal oxide is provided including exposing a heated surface alternately to the vapor of one or more metal amides and then to the vapors of water or an alcohol.

In at least some embodiments, the alcohol is an arene hydrate, or in at least some embodiments, the metal amide or amides are chosen from Table 1.

In another aspect of the invention, a process for forming material including oxygen and one or more metals is provided by exposing a surface alternately to the vapor of one or more organometallic compounds and to the vapor of an arene hydrate.

In at least one embodiment, the organometallic compounds are chosen from Table 2.

BRIEF DESCRIPTION OF THE DRAWINGS

Various objects, features, and advantages of the present invention can be more fully appreciated with reference to the following detailed description of the invention when considered in connection with the following drawings. The drawings are presented for the purpose of illustration only are not intended to be limiting of the invention, in which.

DETAILED DESCRIPTION OF THE INVENTION

Figure 1:
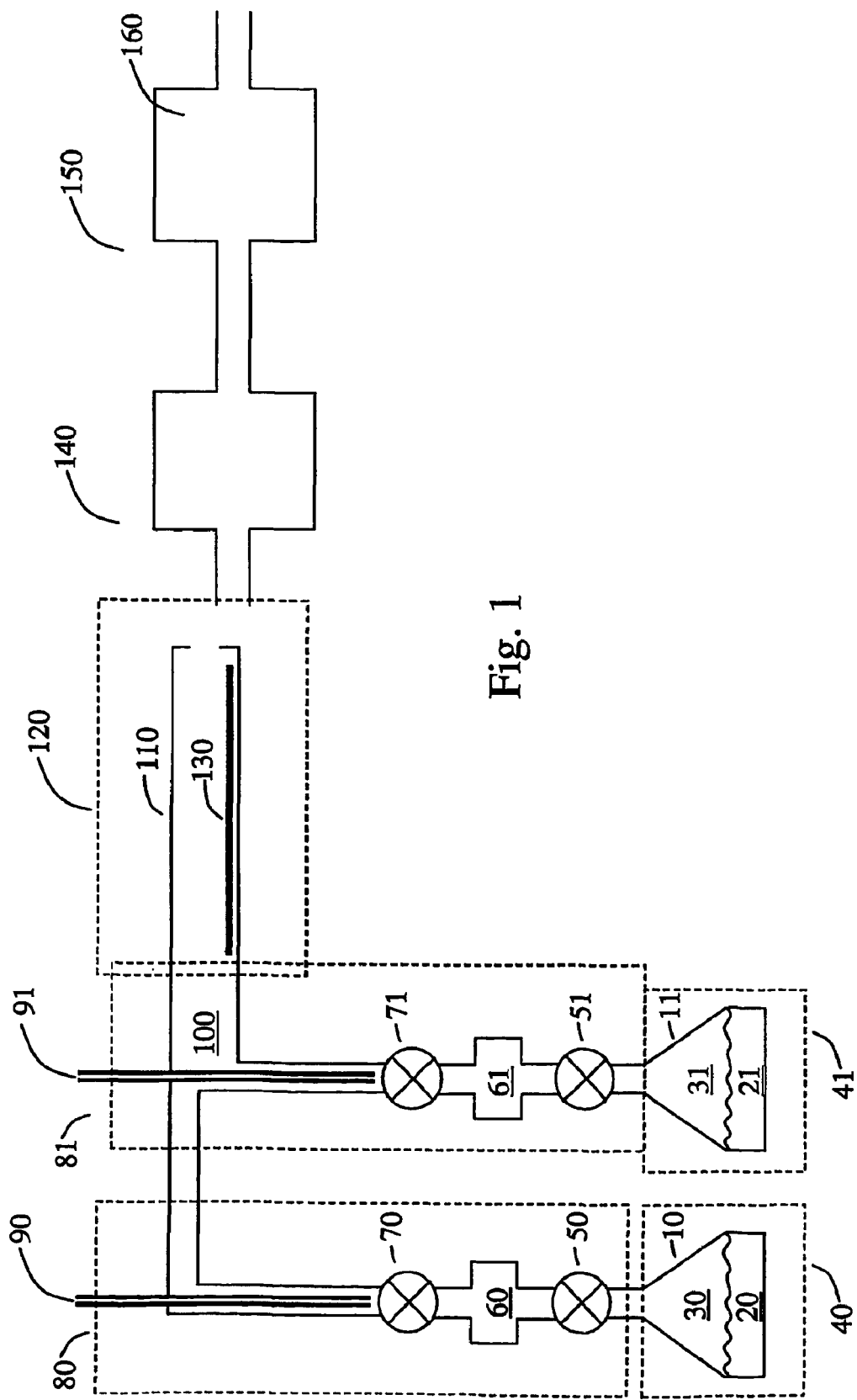
FIG. 1 is a cross-sectional illustration of an atomic deposition layer apparatus used in the practice of at least one embodiment of the invention.

1. Metal Silicates and Silicon Dioxide.

The present invention provides a method for preparing metal silicates of varying metal and silicon content. The method involves the reaction of a vapor of an alkoxysilanol or alkoxysilanediol with a vapor of one or more metal or metalloid compounds. The compound may be formed as a powder or as a film on a substrate, and in some embodiments, on a heated substrate. The compound may be formed on a substrate by mixing the vapors of the alkoxysilanol or alkoxysilanediol and the metal or metalloid compound prior to deposition on a substrate. In at least some embodiments, a substrate is alternately exposed to a alkoxysilanol or alkoxysilanediol vapor and a vapor of one or more of a metal or metalloid compound.

Silanol and silanediol reactants are commercially available or may be prepared using conventional or known techniques. Silicon precursor, tris(tert-butoxy)silanol, is commercially available from Aldrich Chemical Company (Milwaukee, Wis.) and Gelest, Inc. (Tullytown, Pa.). Tris(tert-butoxy)silanol may be prepared as follows. First tris(tert-butoxy)chlorosilane is made by either of the following two reactions:

$$SiCl_4 + 3^tBuOH \rightarrow (^tBuO)_3SiCl + 3HCl \qquad (1)$$

$$SiCl_4 + 3NaO^tBu \rightarrow (^tBuO)_3SiCl + 3NaCl \qquad (2)$$

The tris(tert-butoxy)chlorosilane is then hydrolyzed according to the reaction $$(^tBuO)_3SiCl + H_2O \rightarrow (^tBuO)_3SiOH + HCl \qquad (3)$$

See, Backer et al., *Rec. Trav. Chim.*, volume 61, page 500 (1942). This compound is a solid at room temperature and melts at about 66° C. It sublimes at room temperature at a low pressure of about $10^{-4}$ Torr, and can be distilled at a temperature of about 104° C. at a pressure of 20 Torr. It is highly soluble in organic solvents such as mesitylene or tetradecane, so that its vapors can be formed conveniently by flash vaporization of its solution.

Other tris(tert-alkoxy)silanols may be prepared by similar reactions, by substituting other tertiary alcohols, such as tert-pentyl alcohol (also known as tert-amyl alcohol), for tert-butanol. Tris(tert-amyloxy)silanol, $(^tAmO)_3SiOH$, is a liquid at room temperature, so its vapors can be formed conveniently by flash vaporization of the neat liquid. It has a vapor pressure of about 2 Torr at 96° C. It is commercially available from Aldrich Chemical Company.

Silanols and silanediols may be reacted with a metal source to obtain a metal silicate. The metal source may contain one or more metals and the resultant metal silicate may contain one or more metals, In at least some embodiments, metal compounds include those that react readily with the slightly acidic protons in silanols. These acidic protons are the ones attached directly to oxygen in the silanol. Metal compounds that generally react with these acidic protons include most metal alkyls and other organometallic compounds, metal alkylamides, and some metal alkoxides. The reactivity of any particular compound can be established readily by mixing it with an alkoxysilanol and analyzing the mixture for products by techniques such as nuclear magnetic resonance (NMR). We have found that compounds that are known to react with water also generally react with alkoxysilanols.

The reaction is carried out in the vapor state and may be carried out using CVD or ALD techniques. As is discussed in greater detail below, ALD provides control over the deposition process and is suitable for use in a wide range of reaction conditions and reactant reactivity.

The silicon/metal ratio may be increased by replacing some or all of the metal precursor by a suitably reactive silicon compound. Silicon halides such as silicon tetrachloride, $SiCl_4$, may be used to increase the silicon content, but they may leave chloride as an impurity in the product, and their reactions may be slower than desired. Silicon amides such as tetraisocyanatosilane, tetrakis (dimethylamido)silane or tris(dimethylamido)silane avoid the halogen contamination. However, their deposition rates may also be slower than desired. Silylenes are more rapidly reactive. For example, the thermally stable silylene 7

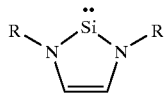

where R is an alkyl group or, in at least some embodiments, is tert-butyl, can be used as a rapidly reacting silicon source in place of part or all of the metal source, in order to increase the silicon/metal ratio.

In at least some embodiments, pure silicon dioxide may be prepared. In an ALD system, a pulse of silylene is followed by a pulse of oxygen gas, in order to fully oxidize the silylene after it has reacted with the surface. Pure silicon dioxide can be deposited rapidly by repeating the pulse sequence of silylene and oxygen.

2. Metal Phosphate and Phosphorus Oxide.

The present invention provides a method for preparing metal phosphates of varying metal and phosphorus content. The method involves the reaction of a vapor of an bis(alkyl) phosphate with a vapor of one or more metal or metalloid compounds. The compound may be formed as a powder or as a film on a substrate, and in some embodiments, on a heated substrate. The compound may be formed on a substrate by mixing the vapors of the bis(alkyl)phosphate and the metal or metalloid compound prior to deposition on a substrate. In at least some embodiments, a substrate is alternately exposed to a bis(alkyl)phosphate vapor and a vapor of one or more of a metal or metalloid compound.

Bis(alkyl)phosphate reactants are commercially available or may be prepared using conventional or known techniques. Phosphorus precursor, diethylphosphate, is commercially available from a number of chemical companies, including Fisher Scientific (Pittsburgh, Pa.) and Pfaltz and Bauer (Waterbury, Conn.). Diethylphosphate may be prepared by the air oxidation of phosphinic acid in ethanol, catalyzed by copper chloride:

$$_2P(O)OH+2EtOH+O_2 \rightarrow (EtO)_2P(O)OH+2H_2O \quad (4)$$

See, Y. Okamoto, T. Kusano and S. Takamuku, *Phosphorus, Sulfur and Silicon*, volume 55, pages 195–200 (1991).

An alternative reaction sequence is shown for diisopropylphosphate and may be used for other precursor compounds by appropriate substitutions for isopropanol.

$$PCl_3+3^iPrOH \rightarrow (^iPrO)_2P(O)H+^iPrCl+2HCl \quad (5)$$

$$(^iPrO)_2P(O)H+SO_2Cl_2 \rightarrow (^iPrO)_2P(O)Cl+HCl+SO_2 \quad (6)$$

$$(^iPrO)_2P(O)Cl+H_2O \rightarrow (^iPrO)_2P(O)OH+HCl \quad (7)$$

See, McIvor et al., *Canadian J. Chemistry*, volume 34, pages 1825 and 1827.

Diisopropylphosphate may also be prepared by first forming its potassium salt by the following two reactions:

$$PCl_3+3^iPrOH \rightarrow (^iPrO)_2P(O)H+^iPrCl+2HCl \quad (8)$$

$$2(^iPrO)_2P(O)H+KMnO_4+KHCO_3 \rightarrow 2(^iPrO)_2P(O)OK+MnO_2 \quad (9)$$

See, A. Zwierak and M. Kiuba, *Tetrahedron*, volume 27, pages 3163 to 3170 (1971).

The analogous sodium salt may be prepared by the following two reactions:

$$POCl_3+3^iPrOH \rightarrow (^iPrO)_3P=O+3HCl \quad (10)$$

$$(^iPrO)_3P=O+NaOH \rightarrow (^iPrO)_2P(O)ONa+^iPrOH \quad (11)$$

The precursor diisopropylphosphate may then be liberated from its alkali salt by reaction with hydrochloric acid:

$$(^iPrO)_2P(O)OM+HCl \rightarrow (^iPrO)_2P(O)OH+MCl, M=Na, K \quad (12)$$

The above bis(alkyl)phosphates react with a wide range of metal compounds to form metal phosphates. Metal compounds that generally react with the acid phosphate protons include most metal alkyls and other organometallic compounds, metal alkylamides, and some metal alkoxides. The reactivity of any particular compound can be established readily by mixing it with a bis(alkyl)phosphate and analyzing the mixture for products by techniques such as nuclear magnetic resonance (NMR).

The reaction is carried out in the vapor state and may be carried out using CVD or ALD techniques. As is discussed in greater detail below, ALD provides control over the deposition process and is suitable for use in a wide range of reaction conditions and reactant reactivity.

The phosphorus/metal ratio may be increased by replacing some or all of the metal precursor by a suitably reactive phosphorus compound. Phosphorus halides such as phosphorus trichloride, $PCl_3$, phosphorus pentachloride, $PCl_5$, or phosphorus oxychloride, $POCl_3$, may be used, but some halogen impurity may be included in the film Phosphorus alkylamides such as hexamethylphosphorus triamide, $(Me_2N)_3P$, hexamethylphosphorimidic triamide, $(Me_2N)_3P$=NH, or hexamethylphosphoramide, $(Me_2N)_3PO$, avoid the halogen contamination, but their reactions may be slow. White phosphorus, $P_4$, and phosphorus(III) oxide, $P_4O_6$, are more quickly reactive and can be used to increase the phosphorus/metal ratio in an ALD process. Doses of white phosphorus or phosphorus(III) oxide generally are followed by a pulse of oxygen in order to form fully oxidized films.

The phosphorus/metal ratio of material made by ALD may be decreased by replacing some of the phosphorus doses by doses of water or alcohol.

3. Metal Amides, Metal Alkyls and Metal Alkoxides.

In at least some embodiments, metal or metalloid amides are useful in the practice of this invention. Some examples are given in Table 1, as well as a commercial source and/or literature references for their synthesis. The metalloids referred to in Table 1 are boron, silicon and arsenic.

TABLE 1

Some Volatile Metal or Metalloid Amides

| Compound | Melt. Pt. °C. | Vapor Press. °C./Torr | Reference and/or commercial source |
|---|---|---|---|
| $Al(N(SiMe_3)_2)_3$ | 188 | | Wannagat, J. Organomet. Chem. 33, 1 (1971) |
| $Al_2(NEt_2)_6$ | liquid | | Barry & Gordon, 2000 |
| $Al_2(NEtMe)_6$ | liquid | 100/0.25 | Barry & Gordon, 2000 |
| $Al(N^iPr_2)_3$ | 56–59 | | Brothers, Organometallics 13, 2792 (1994) |
| $Al_2(NMe_2)_6$ | 88–89 | 90/0.1 | Ruff, JACS 83, 2835 (1961) |
| $Al(N(Et)CH_2CH_2NMe_2)(NMe_2)_2$ | liquid | 65–70/0.3 | Barry, Gordon & Wagner, Mat. Res. Soc. Symp. Proc. 606, 83–89 (2000) |
| $As(NMe_2)_3$ | −53 | 55/10 | Cowley, JACS 95, 6505 (1973) |
| $As(N(Me)(SiMe_3))_3$ | 11–13 | 67–70/0.1 | Birkofer & Ritter, Chem. Ber. 93, 424 (1960) |
| $B(NMe_2)_3$ | −10 | 39/10 | Abel et al., J. Chem. Soc. 1964, 5584 |
| $B(NEt_2)_3$ | | 95/11 | Abel & Armitage J. Organomet. Chem. 5, 326 (1966) |
| $Ba(N(SiMe_3)_2)_2$ | >150 | | Westerhauser, Inorg. Chem. 30, 96 (1991) |
| $Be(NMe_2)_2$ | 88–90 | 175/760 | Anderson, JACS 74, 1421 (1952) |
| $Be(N(SiMe_3)_2)_2$ | −5, liquid | 110/3 | Clark & Haaland, Chem. Commun., 1969, 912 |
| $Be(TMPD)_2$ | −10, liquid | 106/0.001 | Noeth & Schlosser, Inorg. Chem. 22, 2700 (1983) |
| $Bi(N(SiMe_3)_2)_3$ | 90 | | Lappert, J. Chem. Soc., Dalton, 2428 (1980) |
| $Bi(N(Me)(SiMe_3))_3$ | | 90–92/0.1 | Birkofer & Ritter, Chem. Ber. 93, 424 (1960) |
| $Ca(N(SiMe_3)_2)_2$ | >120 | | Lappert, J. Chem. Soc., Chem. Comm., 1141 (1990) |
| $Cd(N(SiMe_3)_2)_2$ | liquid | | Burger, Wannagat, J. Organomet. Chem. 3, 11 (1965) |
| $Cd(N^tBuSiMe_3)_2$ | | | Fisher & Alyea, Polyhedron 3, 509 (1984) |
| $Cd(TMPD)_2$ | | | Fisher & Alyea, Polyhedron 3, 509 (1984) |
| $Ce(N(SiMe_3)_2)_3$ | | 95–100/10$^{-4}$ | Bradley, J. Chem. Soc., Dalton 1973, 1021 |
| $Ce(N^iPr_2)_3$ | | | Angew. Chem., Int. Ed. Engle. 36, 2480 (1997) |
| $Co(N(SiBuMe_2)_2)_2$ | liquid | 146/0.085 | Broomhall-Dillard & Gordon, 1999 |
| $Co(N(SiEtMe_2)_2)_2$ | liquid | 106/0.05 | Broomhall-Dillard & Gordon, 1999 |
| $Co(N(SiMe_3)_2)_2$ | >70 | 50–70/0.01 | Chisholm, CVD 1, 49 (1995) |
| $Co(N(SiMe_3)_2)_3$ | 86–88 | | Power, JACS 11, 8044 (1989) |
| $Co(N(SiPrMe_2)_2)_2$ | liquid | 106/0.05 | Broomhall-Dillard & Gordon, 1999 |
| $Cr(N(SiMe_3)_2)_3$ | 120 | 80/0.005 | Bradley, J. Chem. Soc., Dalton 1972, 1580 |
| $Cr(NEt_2)_4$ | liquid | 40–60/10$^{-3}$ | Bradley, Proc. Chem. Soc., London 1963, 305 |
| $Cr(N^iPr_2)_3$ | | | Bradley & Chisholm, Chem. Comm. 1968, 495 |
| $Cr(NMe_2)_4$ | | | Bradley J. Chem. Soc. A, 1971, 1433 |
| $Cu_4(N(SiMe_3)_2)_4$ | >180(d.) | 160/0.1 | Chisholm, CVD 1, 49 (1995) |
| $Er(N(SiMe_3)_2)_3$ | 150–180 | | Wolczanski, Inorg. Chem. 31, 1311 (1992) |
| $Eu(N(SiMe_3)_2)_3$ | 160–162 | 82–84/10$^{-4}$ | Bradley, Chem. Comm. 1972, 349 |
| $Fe(N(SiBuMe_2)_2)_2$ | liquid | 130/0.2 | Broomhall-Dillard & Gordon, 1999 |
| $Fe(N(SiMe_3)_2)_2$ | 5, liquid | 80–90/0.01 | Chisholm, CVD 1, 49 (1995) |
| $Fe(N(SiMe_3)_2)_3$ | >80 | 80/0.005 | Bradley, J. Chem. Soc., Dalton 1972, 1580 |
| $Ga(NMe_2)_3$ | 91 | 125/0.01 | Chemat Catalog, Northridge, CA |
| $Ga(NEt_2)_3$ | | | Chemat Catalog, Northridge, CA |
| $Ga(N(SiMe_3)_2)_3$ | 187 | | Wannagat, J. Organomet. Chem. 33, 1 (1971) |
| $Ga(N^tBuSiMe_3)_3$ | 174–176 | | Cowley, Inorg. Chem. 33, 3251 (1994) |
| $Ga(TMPD)_3$ | 130–132 | | Cowley, Inorg. Chem. 33, 3251 (1994) |
| $Ga(N(Me)CH_2CH_2NMe_2)(NMe_2)_2$ | liquid | 48–55/0.18 | Barry, Gordon & Wagner, Mat. Res. Soc. Symp. Proc. 606, 83–89 (2000) |
| $Gd(N(SiMe_3)_2)_3$ | 160–163 | 80–83/10$^{-4}$ | Bradley, Chem. Comm. 1972, 349 |
| $Ge(N(SiMe_3)_2)_2$ | 33 | 60/0.04 | Chisholm, CVD 1, 49 (1995) |

TABLE 1-continued

Some Volatile Metal or Metalloid Amides

| Compound | Melt. Pt. °C. | Vapor Press. °C./Torr | Reference and/or commercial source |
|---|---|---|---|
| $Ge(NEt_2)_4$ | >109 | 109/2 | Chemat Catalog, Northridge, CA |
| $Ge(NMe_2)_4$ | 14, liquid | 203/760 | Abel, J. Chem. Soc. 1961, 4933; Chemat |
| $Ge(N^tBu_2)_2$ | 2, liquid | | Lappert, J. Chem. Soc., Chem. Com. 13, 621 (1980) |
| $Ge(N^tBuSiMe_3)_2$ | 22 | 50/0.04 | Lappert, J. Chem. Soc., Dalton Trans. 1977, 2004 |
| $Ge(TMPD)_2$ | 60–62 | 70/0.02 | Lappert, J. Chem. Soc., Chem. Com. 13, 621 (1980) |
| $Hf(NEt_2)_4$ | liquid | 100/0.84 | Bradley, J. Chem. Soc. A, 1969, 980 |
| $Hf(NEtMe)_4$ | liquid | 83/0.05 | Becker & Gordon, 2000; Aldrich |
| $Hf(NMe_2)_4$ | 30 | 70/0.73 | Bradley, J. Chem. Soc. A, 1969, 980 |
| $Hg(N(SiMe_3)_2)_2$ | liquid | | Earborn, J. Chem. Soc., Chem. Comm., 1051 (1968) |
| $Ho(N(SiMe_3)_2)_3$ | 161–164 | $80–85/10^{-4}$ | Bradley, J. Chem. Soc., Dalton 1973, 1021 |
| $In(N(SiMe_3)_2)_3$ | 168 | | Wannagat, J. Organomet. Chem. 33, 1 (1971) |
| $In(TMPD)_3$ | | | Frey et al., Z. Anorg. Allg. Chem. 622, 1060 (1996) |
| $KN(SiHexMe_2)_2$ | liquid | | Broomhall-Dillard, Mater. Res. Soc. 606, 139 (2000) |
| $KN(SiMe_3)_2$ | | $90–100/10^{-3}$ | Fieser & Fieser 4, 407 |
| $La(N(SiMe_3)_2)_3$ | 145–149 | $100/10^{-4}$ | Bradley, J. Chem. Soc., Dalton 1973, 1021 |
| $La(N^tBuSiMe_3)_3$ | 146–147 | $90–95/10^{-4}$ | Becker, Suh & Gordon, 2000 |
| $La(N^iPr_2)_3$ | | | Aspinall, J. Chem. Soc., Dalton 1993, 993 |
| $La(TMPD)_3$ | 137–139 | $100/10^{-4}$ | Suh & Gordon, 2000 |
| $LiN(SiEtMe_2)_2$ | liquid | 123/0.2 | Broomhall-Dillard, Mater. Res. Soc. 606, 139 (2000) |
| $LiN(SiMe_3)_2$ | 71–72 | 115/1 | Inorg. Synth. 8, 19 (1966) |
| Li(TMPD) | | | Kopka, J. Org. Chem. 52, 448 (1987) |
| $Lu(N(SiMe_3)_2)_3$ | 167–170 | $75–80/10^{-4}$ | Bradley, Chem. Comm. 1972, 349 |
| $Mg(N(SiMe_{32})_2$ | 123 | | Andersen, J. Chem. Soc., Dalton Trans. 1982, 887 |
| $Mg(TMPD)_2$ | | | Eaton, JACS 111, 8016 (1989) |
| $Mn(N(SiBuMe_2)_2)_2$ | liquid | 143/0.06 | Broomhall-Dillard & Gordon, 1999 |
| $Mn(N(SiMe_3)_2)_2$ | 55–60 | 112–120/0.2 | Bradley, Trans. Met. Chem. 3, 253 (1978) |
| $Mn(N(SiMe_3)_2)_3$ | 108–110 | | Power, JACS 11, 8044 (1989) |
| $Mo(N^tBuSiMe_3)_3$ | | | Laplaza, Cummins, JACS 118, 8623 (1996) |
| $Mo_2(NEt_2)_6$ | | | Chisholm, JACS 98, 4469 (1976) |
| $Mo_2(NMe_2)_6$ | solid | $100/10^{-4}$ | Chisholm, JACS 98, 4469 (1976) |
| $Mo(NEt_2)_4$ | liquid | $80–110/10^{-4}$ | Bradley & Chisholm, J. Chem. Soc. A 1971, 2741 |
| $Mo(NMe_2)_4$ | solid | 40–70/0.1 | Bradley & Chisholm, J. Chem. Soc. A 1971, 2741 |
| $NaN(Si^nBuMe_2)_2$ | liquid | 189/0.08 | Broomhall-Dillard, Mater. Res. Soc. 606, 139 (2000) |
| $NaN(SiMe_3)_2$ | 171–175 | 170/2 | Chem. Ber. 94, 1540 (1961) |
| $Nb(N(SiMe_3)_2)_3$ | solid | | Broomhall-Dillard & Gordon, 1998 |
| $Nb(NEt_2)_4$ | liquid | | Bradley & Thomas, Can. J. Chem. 40, 449 (1962) |
| $Nb(NEt_2)_5$ | >120 | 120/0.1 | Bradley & Thomas, Can. J. Chem. 40, 449 (1962) |
| $Nb(NMe_2)_5$ | >100 | 100/0.1 | Bradley & Thomas, Can. J. Chem. 40, 449 (1962) |
| $Nd(N(SiMe_3)_2)_3$ | 161–164 | $85–90/10^{-4}$ | Bradley, J. Chem. Soc., Dalton 1973, 1021 |
| $Nd(N^iPr_2)_3$ | | | Bradley, Inorg. Nucl. Chem. Lett. 12, 735 (1976) |
| $Ni(N(SiMe_3)_2)_2$ | liquid | 80/0.2 | Burger & Wannagat, Mh. Chem. 95, 1099 (1964) |
| $Pb(N(SiMe_3)_2)_2$ | 39 | 60/0.04 | Lappert, J. Chem. Soc., Chem. Com. 16, 776 (1980) |
| $Pb(N^tBuSiMe_3)_2$ | 22 | 50/0.04 | Lappert, J. Chem. Soc., Dalton Trans. 1977, 2004 |
| $Pr(N(SiMe_3)_2)_3$ | 155–158 | $88–90/10^{-4}$ | Bradley, Chem. Comm. 1972, 349 |
| $Sb(NMe_2)_3$ | liquid | 50/0.5 | Cowley, JACS 95, 6506 (1973) |
| $Sb(N(Me)(SiMe_3))_3$ | 9–11 | 78–79/0.1 | Birkofer & Ritter, Chem. Ber. 93, 424 (1960) |
| $Sc(N(SiMe_3)_2)_3$ | 172–174 | | Bradley, J. Chem. Soc., Dalton 1972, 1580 |
| $SiH_2(NMe_2)_2$ | −104 | 93/760 | Anderson et al., J. Chem. Soc. Dalton 12, 3061 (1987) |
| $SiH(NMe_2)_3$ | −90 | 62/45 | Gelest, Pfaltz & Bauer, Strem Catalogs |
| $Si(NMe_2)_4$ | 1–2 | 196/760 | Gordon, Hoffman & Riaz, Chem. Mater. 2, 480 (1990) |
| $Si(NHMe)_4$ | 37 | 45/0.05 | Schmisbaur, Inorg. Chem. 37, 510 (1998) |

TABLE 1-continued

Some Volatile Metal or Metalloid Amides

| Compound | Melt. Pt. °C. | Vapor Press. °C./Torr | Reference and/or commercial source |
|---|---|---|---|
| Si(NHn-Pr)$_4$ | liquid | 75/0.05 | Schmisbaur, Inorg. Chem. 37, 510 (1998) |
| Si(NEt$_2$)$_4$ | 3–4 | 74/19 | Abel et al, J. Chem. Soc. 1965, 62; Chemat |
| Si(NCO)$_4$ | 25–26 | 40/1 | Forbes & Anderson, JACS 62, 761 (1940); Gelest, Petrarch, Showa-Denko |
| Si(NCO)$_4$ | 25–26 | 40/1 | Forbes & Anderson, JAGS 62, 761 (1940); Gelest, Petrarch, Showa-Denko |
| Sm(N(SiMe$_3$)$_2$)$_3$ | 155–158 | 83–84/10$^{-4}$ | Bradley, Chem. Comm. 1972, 349 |
| Sn(N(SiMe$_3$)$_2$)$_3$ | 38 | 84/0.04 | Chisholm, CVD 1, 49 (1995) |
| Sn(NEt$_2$)$_4$ | liquid | 90/0.05 | Jones & Lappert, J. Chem. Soc. 1965, 1944 |
| Sn(NMe$_2$)$_4$ | liquid | 51/0.15 | Jones & Lappert, J. Chem. Soc. 1965, 1944 |
| Sn(N$^t$Bu$_2$)$_2$ | 47 | | Lappert, J. Chem. Soc., Chem. Com. 13, 621 (1980) |
| Sn(N$^t$Bu$_2$)$_3$ | | | Hudson, J. Chem. Soc., Dalton Trans. 1976, 2369 |
| Sn(N$^t$BuSiMe$_3$)$_2$ | 19, liquid | 50/0.04 | Lappert, J. Chem. Soc., Dalton Trans. 1977, 2004 |
| Sn(N$^t$BuSiMe$_3$)$_3$ | | | Hudson, J. Chem. Soc., Dalton Trans. 1976, 2369 |
| Sn(TMPD)$_2$ | | | Lappert, J. Chem. Soc., Chem. Com. 16, 776 (1980) |
| Sr(N(SiMe$_3$)$_2$)$_2$ | 164 | | Westerhauser, Inorg. Chem. 30, 96 (1991) |
| Ta(NEt$_2$)$_4$ | | 120/0.1 | Bradley & Thomas, Can. J. Chem. 40, 1355 (1962) |
| Ta(NMe$_2$)$_5$ | >180 | 100/0.1 | Bradley & Thomas, Can. J. Chem. 40, 1355 (1962); Strem |
| Ta(N$^t$Bu)(NEt$_2$)$_3$ | liquid | 90/0.1 | Inorgtech |
| Ta(NEt)(NEt$_2$)$_3$ | liquid | 120/0.1 | Becke-Goehring & Wunsch, Chem. Ber. 93, 326 (1960) |
| Tb(N(SiMe$_3$)$_2$)$_3$ | 162–165 | 78–82/10$^{-4}$ | Wolczanski, Inorg. Chem. 31, 1311 (1992) |
| Th(NEt$_2$)$_4$ | | 40–50/10$^{-4}$ | Reynolds & Edelstein, Inorg. Chem. 16, 2822 (1977) |
| Th(NPr$_2$)$_4$ | liquid | 60–70/10$^{-4}$ | Reynolds & Edelstein, Inorg. Chem. 16, 2822 (1977) |
| Ti(N(SiMe$_3$)$_2$)$_3$ | solid | | Bradley, J. Chem. Soc., Dalton 1972, 1580 |
| Ti(NEt$_2$)$_4$ | liquid | 112/0.1 | Bradley & Thomas, J. Chem. Soc. 1960, 3857 |
| Ti(N$^i$Pr$_2$)$_3$ | | | Kruse, Inorg. Chem. 9, 2615 (1970) |
| Ti(N$^i$Pr$_2$)$_4$ | 82–85 | 110/0.001 | Froneman, P, S, Si, Relat. Elem. 47, 273 (1990) |
| Ti(NMe$_2$)$_4$ | liquid | 50/0.05 | Bradley & Thomas, J. Chem. Soc. 1960, 3857 |
| Tl(N(SiMe$_3$)$_2$)$_3$ | | | Allman, J. Organomet. Chem. 162, 283 (1978) |
| U(N(SiMe$_3$)$_2$)$_3$ | 137–140 | 80–100/10$^{-3}$ | Andersen, Inorg. Chem. 18, 1507 (1979) |
| U(NEt$_2$)$_4$ | | 115–125/1.06 | Jones, JACS 78, 4285 (1956) |
| U(NPr$_2$)$_4$ | liquid | 40–50/10$^{-4}$ | Reynolds & Edelstein, Inorg. Chem. 16, 2822 (1977) |
| V(N(SiMe$_3$)$_2$)$_3$ | >95 | 95/0.005 | Bradley, J. Chem. Soc., Dalton 1972, 1580 |
| V(NEt$_2$)$_4$ | liquid | 90/0.001 | Bradley, Chem. Commun. 1964, 1064 |
| V(NMe$_2$)$_4$ | solid | 50/0.001 | Bradley, J. Chem. Soc. A, 1969, 2330 |
| V(O)(NMe$_2$)$_3$ | 40 | 40/0.001 | Davidson, Harris & Lappert, JCS Dalton 1976, 2268 |
| W$_2$(NEt$_2$)$_6$ | solid | 140–170/10$^{-4}$ | Chisholm, JACS 97, 5626 (1975); 98, 4477 (1976) |
| W$_2$(NMeEt)$_6$ | solid | 100–130/10$^{-4}$ | Burger & Wannagat, Monatsh. 95, 1099 (1964) |
| W$_2$(NMe$_2$)$_6$ | solid | 100–120/10$^{-4}$ | Burger & Wannagat, Monatsh. 95, 1099 (1964) |
| W(N$^t$Bu)$_2$(NH$^t$Bu)$_2$ | 89–90 | 60–65/10$^{-4}$ | Nugent & Harlow, Inorg. Chem. 19, 777 (1980) |
| W(N$^t$Bu)$_2$(NEtMe)$_2$ | liquid | 87/0.1 | Suh & Gordon, 2000 |
| W(N$^t$Bu)$_2$(NMe$_2$)$_2$ | liquid | 75/0.1 | Suh & Gordon, 2000 |
| Y(N(SiMe$_3$)$_2$)$_3$ | 180–184 | 100/10$^{-4}$ | Bradley, J. Chem. Soc., Dalton 1973, 1021; Alfa |
| Y(N$^i$Pr$_2$)$_3$ | | | Bradley, Inorg. Nucl. Chem. Lett. 12, 735 (1976) |
| Y(N$^t$BuSiMe$_3$)$_3$ | 158–160 | 90–95/10$^{-4}$ | Suh & Gordon, 2000 |
| Y(TMPD)$_3$ | 177–179 | 100/10$^{-4}$ | Suh & Gordon, 2000 |
| Yb(N(SiMe$_3$)$_2$)$_3$ | 162–165 | | Bradley, J. Chem. Soc., Dalton 1973, 1021 |
| Yb(N$^i$Pr$_2$)$_3$ | | | Bradley, Inorg. Nucl. Chem. Lett. 12, 735 (1976) |
| Zn(N(SiMe$_3$)$_2$)$_2$ | liquid | 120/0.1 | Inorg. Chem. 23, 1972 (1984) |
| Zn(N$^t$Bu$_2$)$_2$ | | | Schumann, Z. Anorg. Allg. Chem. 623, |

TABLE 1-continued

Some Volatile Metal or Metalloid Amides

| Compound | Melt. Pt. ° C. | Vapor Press. ° C./Torr | Reference and/or commercial source |
|---|---|---|---|
| Zn(TMPD)$_2$ | | | 1881 (1997)<br>Schumann, Z. Anorg. Allg. Chem. 623, 1881 (1997) |
| Zr(NEt$_2$)$_4$ | liquid | 112/0.1 | Bradley & Thomas, J. Chem. Soc. 1960, 3857 |
| Zr(NEtMe)$_4$ | liquid | 82/0.05 | Becker & Gordon, 2000 |
| Zr(N$^i$Pr$_2$)$_4$ | >120 | 120/0.001 | Bradley, Inorg. Nucl. Chem. Lett. 11, 155 (1975) |
| Zr(NMe$_2$)$_4$ | 70 | 65–80/0.1 | Bradley & Thomas, J. Chem. Soc. 1960, 3857 |

In Table 1, TMPD stands for 2,2,6,6-tetramethylpiperidide. Further examples may be found in the book Metal and Metalloid Amides, by M. F. Lappert, P. P. Power, A. R. Sanger and R. C. Srivastava, published in 1980 by Ellis Horwood Ltd., a division of John Wiley & Sons.

In at least some embodiments, metal alkyls are useful in the practice of this invention. Some examples are given in Table 2, as well as a commercial source or literature reference of their synthesis.

TABLE 2

Some Volatile Organometallic Compounds

| Compound | Melt. Pt. ° C. | Vapor Press. C./Torr | Sources |
|---|---|---|---|
| AlMe$_3$ | 15.4 | 20/8 | Strem |
| Ba(n-PrMe$_4$Cp)$_2$ | liquid | | Strem |
| Ba($^i$Pr$_4$Cp)$_2$ | 149–150 | 90/0.01 | J. Am. Chem. Soc. 113, 4843–4851 (1991) |
| Ba(Me$_5$Cp)$_2$ | 265–268 | 140/0.01 | J. Organomet. Chem. 325, 31–37 (1987) |
| BeEt$_2$ | 12, liquid | 110/15 | Strem |
| BiMe$_3$ | liquid | 110/760 | Pfaltz & Bauer, Organometallics |
| Ca($^i$Pr$_4$Cp)$_2$ | 196–200 | 190/0.01 | J. Am. Chem. Soc. 113, 4843–4851 (1991) |
| Ca(Me$_5$Cp)$_2$ | 207–210 | 90/0.01 | J. Organomet. Chem. 325, 31–37 (1987) |
| CdMe$_2$ | −4.5 | 105.5/760 | Strem |
| CeCp$_3$ | 452 | 230/0.01 | Strem |
| Ce($^i$PrCp)$_3$ | | | Strem |
| Ce(Me$_4$Cp)$_3$ | solid | | Aldrich |
| CoCp$_2$ | 176–180 | | Aldrich, Strem |
| CoCp(CO)$_2$ | liquid | 37–38.5/2 | Strem |
| Co(CO)$_3$NO | liquid | 50/760 | Strem |
| CrCp$_2$ | 168–170 | | Aldrich, Strem |
| Cr(Me$_5$Cp)$_2$ | 200 | | Strem |
| Cr($^i$PrCp)$_2$ | solid | | Strem |
| Cr(EtBz)$_2$ | liquid | 140–160/1 | Strem |
| CuCpPEt$_3$ | solid | 60/0.01 | Strem |
| Er(Cp)$_3$ | 285 | 200/0.01 | Strem |
| Er($^i$PrCp)$_3$ | 63–65 | 222/10 | Aldrich, Alfa, Strem |
| Er(BuCp)$_3$ | liquid | 240/0.1 | Aldrich, Alfa (pyrophoric) |
| Eu(Me$_4$Cp)$_3$ | solid | | Aldrich |
| FeCp(Me$_2$NCH$_2$Cp) | liquid | 91–92/0.5 | Strem |
| FeCp($^t$BuCp) | liquid | 80/0.15 | Strem |
| GaMe$_3$ | −15, liquid | 55.7/760 | Strem |
| GdCp$_3$ | 295 | | Aldrich, Alfa, Strem |
| Gd($^i$PrCp)$_3$ | liquid | 200/0.01 | Erbil, U.S. Pat. No. 4,882,206 (1989) |
| InCp$_3$ | solid | 50/0.01 | Strem |
| In(Me$_5$Cp)$_3$ | | | Strem |
| InMe$_3$ | 88 | | Strem |
| Ir(MeCp)(1,5-COD) | | | Strem |
| La($^i$PrCp)$_3$ | liquid | 180–195/0.01 | Strem; Erbil, U.S. Pat. No. 4,882,206 (1989) |
| LaCp$_3$ | 295 dec. | 218/0.1 | Aldrich, Alfa, Strem |
| LaCp$_3$(NCCH$_3$)$_2$ | 162 | | Inorganica Chim. Acta 100, 183–199 (1985) |
| La(Me$_2$NC$_2$H$_4$Cp)$_3$ | 75 | 160/0.001 | J. Organomet. Chem. 462, 163–174 (1993) |
| Mg(PrCp)$_2$ | liquid | | Strem |
| Mg(EtCp)$_2$ | liquid | | Aldrich, Strem |
| MgCp$_2$ | 180 | 160/0.1 | Aldrich, Strem |

TABLE 2-continued

Some Volatile Organometallic Compounds

| Compound | Melt. Pt. ° C. | Vapor Press. ° C./Torr | Sources |
|---|---|---|---|
| $MnCp_2$ | 175 | | Aldrich, Strem |
| $Mn(EtCp)_2$ | liquid | | Aldrich (pyrophoric) |
| $Mn(Me_5Cp)_2$ | 292 | | Strem |
| $Mo(EtBz)_2$ | liquid | | Strem |
| $NdCp_3$ | 417 | 220/0.01 | Aldrich, Alfa, Strem |
| $Nd(^iPrCp)_3$ | solid | | Aldrich, Alfa, Strem |
| $Ni(PF_3)_4$ | liquid | 70.7/760 | Strem |
| $PrCp_3$ | 427 | 220/0.01 | Aldrich, Alfa, Strem |
| $Pr(^iPrCp)_3$ | 50–54 | | Aldrich, Alfa, Strem |
| $SbEt_3$ | | 156/760 | Strem |
| $ScCp_3$ | 240 | 200/0.05 | Aldrich, Strem |
| $SmCp_3$ | 356 | 220/0.01 | Strem |
| $Sm(^iPrCp)_3$ | | | Zh. Neorg. Khim. 27, 2231–4 (1982) |
| $Sr(^iPr_4Cp)_2$ | 151–153 | | Chem. Rev. 93, 1023-1–36 (1993) |
| $Sr(Me_5Cp)_2$ | 216–218 | | J. Organomet. Chem. 325, 31–37 (1987) |
| $Tb(^iPrCp)_3$ | solid | | Aldrich, Strem |
| $TmCp_3$ | solid | | Strem |
| $Tm(^iPrCp)_3$ | | | MRS Symp. Proc. 301, 3–13 (1993) |
| $TlCp$ | solid | 75/0.1 | Strem |
| $VCp_2$ | 165–167 | 200/0.1 | Aldrich, Strem |
| $V(EtCp)_2$ | liquid | | Aldrich |
| $W(^iPrCp)_2H_2$ | liquid | 122–125/0.1 | Aldrich, Strem |
| $YCp_3$ | 296 | 200/2 | Alfa, Strem |
| $Y(MeCp)_3$ | | | Strem |
| $Y(^nPrCp)_3$ | | | Strem |
| $Y(BuCp)_3$ | liquid | | Aldrich, Alfa, Strem |
| $YbCp_3$ | 277 | 150(vac.) | Strem |
| $Yb(^iPrCp)_3$ | 47 | | Zh. Neorg. Khim. 27, 2231–4 (1982) |
| $ZnEt_2$ | −28, liquid | 124/760 | Aldrich, Strem |
| $ZnMe_2$ | −42, liquid | 46/760 | Aldrich, Strem |
| $ZrCp_2Me_2$ | 170 | | Aldrich, Strem |
| $Zr(^tBuCp)_2Me_2$ | | | Strem |

In Table 2, Cp is an abbreviation for cyclopentadienide, $Me_5Cp$ represents pentamethylcyclopentadienide, $^iPrCp$ represents isopropylcyclopentadienide, $^iPrMe_4Cp$ stands for isopropyltetramethylcyclopentadienide, $^iPr_4Cp$ stands for tetraisopropylcyclopentadienide, EtCp stands for ethylcyclopentadienide, PrCp stands for propylcyclopentadienide, $^iPrCp$ stands for isopropylcyclopentadienide, BuCp stands for butylcyclopentadienide, Bz for benzenide, EtBz for a mixture of isomers of ethylbenzenide and 1,5-COD for 1,5-cyclooctadienide.

In at least some embodiments, metal or metalloid alkoxides can be used in the practice of this invention. Suitable compounds are listed in Table 3, as well as a commercial source or a literature reference of their synthesis.

TABLE 3

Some Volatile Metal or Metalloid Alkoxides

| Compound | Melt. Pt. ° C. | Vapor Press. ° C./Torr | Sources |
|---|---|---|---|
| $Al_2Et_3(O\text{-sec-Bu})_3$ | liquid | 190/0.1 | Strem |
| $B(OMe)_3$ | −29, liquid | 68.7/760 | Aldrich, Rohm and Haas, Strem |
| $Hf(O^tBu)_4$ | liquid | 90/5 | Strem |
| $Nb(OEt)_5$ | 6, liquid | 156/0.05 | Aldrich, Chemat, Strem |
| $Ta(OEt)_5$ | 21 | 146/0.15 | Aldrich, Chemat, Strem |
| $Ti(O^iPr)_4$ | 20 | 58/1 | Aldrich, Chemat, DuPont, Strem |
| $Y(OCMe_2CH_2NMe_2)_3$ | liquid | 80/0.001 | Herrmann, Inorg. Chem. 36, 3545–3552(1997) |
| $Zr(O^tBu)_4$ | liquid | 81/3, 90/5 | Aldrich, Strem |

Metal halides may also be used in the practice of this invention, but they have the disadvantages that they tend to leave some halide impurity in the film and cause corrosion of substrates or apparatus.

4. Reactions with Water and Alcohols.

In at least some embodiments, part of the silanol or phosphate is replaced with water in order to deposit metal-rich silicates and phosphates. In a CVD reactor, water vapor tends to react very quickly with the vapors of the metal precursors near the vapor entrance to produce powder, rather than film on the substrate. In an ALD reactor such premature reactions are avoided because the reactants are introduced alternately into the reactor, so reactions near the entrance are prevented and reaction is confined to the surface of the substrate. However, water tends to adsorb strongly on surfaces, so it can take a long time to purge the ALD reactor between pulses of the reactants.

Alcohols such as isopropanol and tert-butanol can alleviate these problems with water, since the reactions of alcohols with metal compounds are slower, and the more volatile alcohols can be pumped more quickly from an ALD reactor. Alcohols such as isopropanol and tert-butanol are particularly appropriate for reactions involving thermally liable metal compounds. In some cases the substrate temperature is raised in order to decompose alkyl alcohols and thereby remove their carbon content from the film. A thermally labile metal compound may self-decompose at higher substrate temperatures, so self-limiting ALD reactions cannot be achieved.

The arene hydrates are a class of alcohols that decompose at lower temperatures than ordinary alkyl alcohols, and thus can be used to provide carbon-free metal oxides at low enough temperatures to avoid self-decomposition of even thermally labile metal compounds. For example, benzene hydrate decomposes easily to water and benzene because of the aromatic stabilization of the benzene byproduct:

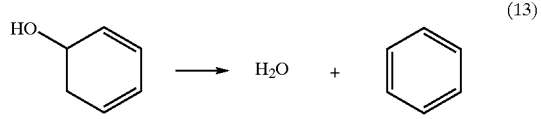
(13)

Other examples of useful arene hydrates are alkyl-substituted benzene hydrates such as the various isomers of toluene hydrate:

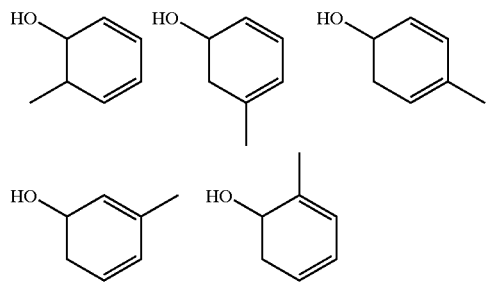

Other useful alcohols include the two naphthalene hydrates

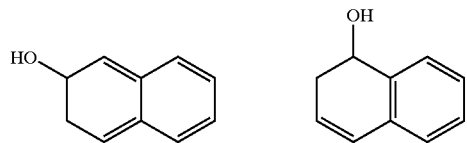

and alkyl-substituted naphthalene hydrates such as methyl naphthalene hydrate. Thus arene alcohols may be used in the reaction of metal compounds at moderate deposition conditions. In particular, it can be used for the formation of metal oxides, or for the formation of metal silicates or metal phophates when used in combination with the silicon and phosphorus precursors described herein.

In at least some embodiments of the present invention, a metal oxide is obtained by reaction of a metal amide with water. Suitable metal amides include any of those listed in Table 1. Thus, by way of example, hafnium oxide was prepared by ALD using water vapor and tetrakis (dimethylamido)hafnium. This ALD reaction was found to be surprisingly efficient, in that almost all of the precursor that was delivered into the reaction chamber was deposited as film on the substrate and on the exposed wall of the chamber. It was also found to be surprisingly fast, going to completion (saturation of the surface reaction on a flat surface) with less than 50 Langmuirs of vapor flux (1 Langmuir is the flux delivered to a surface in one second by a partial pressure of $10^{-6}$ Torr of the precursor). The byproducts of the reaction were found to consist of dimethylamine vapor, which does not etch the deposited hafnium oxide film. Most surprisingly, the use of tetrakis (alkylamido)hafnium precursors succeeded in the ALD of highly uniform films of hafnium oxide even in holes with very high aspect rations (over 40). By way of contrast, the reactants commonly used in the prior art for ALD of hafnium oxide, $HfCl_4$ and $Hf(O\text{-tert-Bu})_4$, have not succeeded in the uniform deposition of $HfO_2$ in holes with such high aspect ratios.

5. Vaporization of Reactants and Product Deposition.

Vapors of liquid precursors may be formed by conventional methods, including heating in a bubbler, in a thin-film evaporator, or by nebulization into a carrier gas preheated to about 100 to 250° C. The nebulization may be carried out pneumatically or ultrasonically. Solid precursors may be dissolved in organic solvents, including hydrocarbons such as decane, dodecane, tetradecane, toluene, xylene and mesitylene, and with ethers, esters, ketones and chlorinated hydrocarbons. Solutions of liquid precursors generally have lower viscosities than the pure liquids, so that in some cases it may be preferable to nebulize and evaporate solutions rather than the pure liquids. The liquids or solutions can also be evaporated with thin-film evaporators or by direct injection of the liquids into a heated zone. Thin-film evaporators are made by Artisan Industries (Waltham, Mass.). Commercial equipment for direct vaporization of liquids is made by MKS Instruments (Andover, Mass.), ATMI, Inc. (Danbury, Conn.), Novellus Systems, Inc. (San Jose, Calif.) and COVA Technologies (Colorado Springs, Colo.). Ultrasonic nebulizers are made by Sonotek Corporation Milton, N.Y.) and Cetac Technologies (Omaha, Nebr.).

The silicon precursors of the present invention may be reacted with metal or metalloid amides, such as those in Table 1, to form metal or metalloid silicates. The silicon precursors of the present invention may be reacted with organometallic compounds, such as those in Table 2, to form metal silicates. The silicon precursors of the present invention may be reacted with metal or metalloid alkoxides, such as those in Table 3, to form metal or metalloid silicates. The silicon precursors of the present invention may also be reacted with other suitably reactive metal compounds to form metal silicates. For example, tris(tert-butoxy)silanol may be reacted with tris(tert-butyl(trimethylsilyl)amido) yttrium (Table 1) to form yttrium silicate (Examples 5 and 6). Also, tris(tert-butoxy)silanol may be reacted with tris (tert-butyl(trimethylsilyl)amido)lanthanum (Table 1) to form lanthanum silicate (Examples 7 and 8). Metal oxides may be obtained by reactin of a suitable metal and with water. Tris(bis(trimethylsilyl)amido)lanthanum reacts with water vapor to form a more lanthanum-rich silicate (Example 21). Lanthanum oxide may be deposited from silicon-free precursors such as tris(2,2,6,6-tetramethylpiperidido)lanthanum (Example 22).

The phosphorus precursors of the present invention may be reacted with suitably reactive metal compounds, such as those in the Tables, to form metal phosphates. For example, diisopropylphosphate may be reacted with lithium bis (ethyldimethylsilyl)amide (Table 1) to provide a process for depositing lithium phosphate films that are lithium ion conductors, as is shown in Examples 9 and 10.

The process of the invention can be carried out in standard equipment well known in the art of chemical vapor deposition (CVD). The CVD apparatus brings the vapors of the reactants into contact with a heated substrate on which the material deposits. A CVD process can operate at a variety of pressures, including in particular normal atmospheric pressure, and also lower pressures. Commercial atmospheric pressure CVD furnaces are made in the USA by the Watkins-Johnson Company (Scotts Valley, Calif.), BTU International (North Billerica, Mass.) and SierraTherm (Watsonville, Calif.). Commercial atmospheric pressure CVD equipment for coating glass on the float production line is made in the USA by Pilkington North America (Toledo, Ohio), PPG Industries (Pittsburgh, Pa.) and AFG Industries (Kingsport, Tenn.). Low-pressure CVD equipment is made by Applied Materials (Santa Clara, Calif.), Spire Corporation (Bedford, Mass.), Materials Research Corporation (Gilbert, Ariz.), Novellus Systems, Inc. (San Jose, Calif.), Genus (Sunneyvale, Calif.), Mattson Technology (Frement, Calif.), Emcoie Corporation (Somerset, N.J.), NZ Applied Technologies (Woburn, Mass.), COVA Technologies (Colorado Springs, Colo.) and CVC Corporation (Freemont, Calif.). Apparatus adapted to atomic layer deposition (ALD) is available from Genus (Sunneyvale, Calif.) and ASM Microchemistry (Espoo, Finland).

The process of the invention may also be carried out using atomic layer deposition (ALD). ALD introduces a metered amount of a first reactant component into a deposition chamber having a substrate therein for layer deposition. A thin layer of the first reactant is deposited on the substrate. After a preselected time period, a metered amount of a second reactant component is then introduced into the deposition chamber, which is deposited on and interacts with the already deposited layer of the first reactant component. Alternating layers of first and second reactant components are introduced into the deposition chamber and deposited on the substrate to form a layer of controlled composition and thickness. Alternation of deposition may be on the order of seconds to minutes and is selected to provide adequate time for the just introduced component to deposit on the substrate and for any excess vapor to be removed from the headspace above the substrate. It has been determined that the surface reactions are self-limiting so that a reproducible layer of predictable composition is deposited. Use of more than two reactant components is within the scope of the invention.

In at least some embodiments of the invention, automobile fuel injectors (Ford model CM-4722 F13Z-9F593-A) may be used to deliver pulses of the solutions of precursors into the nitrogen carrier gas. Solution is delivered each time a valve opens for about 50 milliseconds.

In another embodiment of the invention, 6-port sampling valves (Valco model EP4C6WEPH, Valco Instruments, Houston, Tex.) normally used for injecting samples into gas chromatographs may be used to deliver pulses of solutions into a suitable carrier gas. Each time that a valve is opened, solution flows into a tube in which solution is vaporized by heat from hot oil flowing over the outside of the tube. Carrier gas moves the vapor from the tube into the ALD reactor tube.

In at least some embodiments, a layer is deposited by ALD using an apparatus such as that illustrated in FIG. 1. According to at least some embodiments, measured doses of reactant vapor 30 are introduced into the heated deposition chamber 110 by the use of a pair of air-actuated diaphragm valves, 50 and 70 (Titan II model made by Parker-Hannifin, Richmond Calif.). The valves are connected by a chamber 60 having a measured volume V, and this assembly is placed inside an oven 80 held at a controlled temperature $T_2$. The pressure of the reactant vapor 30 in the precursor reservoir 10 is equal to the equilibrium vapor pressure $P_{eq}$ of the solid or liquid reactant 20 at a temperature $T_1$ determined by the surrounding oven 40. The temperature $T_1$ is chosen to be high enough so that the precursor pressure $P_{eq}$ is higher than the pressure $P_{dep}$ in the deposition chamber. The temperature $T_2$ is chosen to be higher than $T_1$ so that only vapor and no condensed phase is present in the valves 50 and 70 or the chamber 60. In the case of a gaseous reactant, its pressure can be set by a pressure regulator (not shown) that reduces its pressure from the pressure in the precursor gas cylinder 10.

A similar arrangement is provided for each reactive precursor introduced into the deposition chamber 110. Thus, a precursor reservoir 11 holds a solid or liquid reactant 21 having a vapor pressure 31 at a temperature $T_1'$ maintained by surrounding oven 41. Valves 51 and 71 are connected by a chamber 61 having a measured volume V' and this assembly is housed in oven 81 at temperature $T_2'$.

Carrier gas (such as nitrogen) flows at a controlled rate into inlet 90 in order to speed the flow of the reactants into the deposition chamber and the purging of reaction byproducts and un-reacted reactant vapor. A static mixer may be placed in the tubing 100 leading into the reactor, to provide a more uniform concentration of the precursor vapor in the carrier gas as it enters the deposition chamber 110 heated by furnace 120 and containing one or more substrates 130. The reaction byproducts and un-reacted reactant vapors are removed by trap 140 before passing into a vacuum pump 150. Carrier gas exits from exhaust 160.

In operation, valve 70 is opened so that the pressure inside chamber 60 is reduced to a value $P_{dep}$ close to that of the deposition chamber 110. Then valve 70 is closed and valve 50 is opened to admit precursor vapor from precursor reservoir 10 into chamber 60. Then valve 50 is closed so that the volume V of chamber 60 contains vapor of the precursor at a pressure $P_{eq}$. Finally, valve 70 is opened to admit most of the precursor vapor contained in chamber 60 into the deposition chamber. The number of moles, n, of precursor delivered by this cycle can be estimated by assuming that the vapor obeys the ideal gas law:

$$n=(P_{eq}-P_{dep})(V/RT_1) \quad (14)$$

where R is the gas constant. This expression also assumes that carrier gas from tube 90 does not enter chamber 60 through valve 70 during the brief time that it is open to release the precursor vapor. If mixing of carrier gas with the precursor vapor does occur during the time that valve 70 is open, then a larger dose of precursor vapor may be delivered, up to a maximum value $$n=(P_{eq})(V/RT_1) \quad (15)$$

if all the residual precursor vapor in chamber 60 is displaced by carrier gas. For precursors with relatively high vapor pressure ($P_{eq}>>P_{dep}$), there is not much difference between these two estimates of the precursor dose.

This cycle of delivering precursor 20 is repeated if necessary until the required dose of precursor 20 has been delivered into reaction chamber. Normally, in an ALD process, the dose of precursor 20 delivered by this cycle (or several such cycles repeated to give a larger dose) is chosen to be large enough to cause the surface reactions to go to completion (also called "saturation").

Next a dose of vapor 31 from a second precursor 21 may be measured and delivered by a similar apparatus with components numbered similarly to the apparatus for the first precursor 20.

In the case of precursors with vapor pressure so low that $P_{eq}$ is less than $P_{dep}$, this method will not deliver any precursor vapor into the deposition chamber. The vapor pressure can be increased by raising the temperature $T_1$, but in some cases a higher temperature would result in thermal decomposition of the precursor. In such cases of thermally sensitive precursors with low vapor pressure, vapor may be delivered using the apparatus in FIG. 2. The chamber 220 is first pressurized with carrier gas delivered through tube 240 and valve 200 from a pressure controller (not shown). Valve 200 is then closed and valve 210 opened to allow the carrier gas to pressurize precursor reservoir 220 to pressure $P_{tot}$. The mole fraction of precursor vapor in the vapor space 30 of reservoir 10 is then $P_{eq}/P_{tot}$. If $P_{tot}$ is set to a pressure larger than the pressure $P_{dep}$ in the deposition chamber, then the number of moles delivered in a dose can be estimated from the equation $$n=(P_{eq}/P_{tot})(P_{tot}-P_{dep})(V/RT_1) \qquad (16)$$

where V is the volume of the vapor space 30 in chamber 10. This dose is delivered by opening valve 230. If carrier gas from tube 90 enters the volume 30 during the time that the valve 230 is open, then a dose somewhat larger than this estimate may be delivered. By making the volume V large enough, a precursor dose that is certainly large enough to saturate the surface reaction may be delivered. If the vapor pressure $P_{eq}$ is so low that the required volume V would be impracticably large, then additional doses from volume V may be delivered before delivering a dose of the other reactant.

A similar apparatus is provided for each precursor reactant of the system. Thus, chamber 221 is first pressurized with carrier gas delivered through tube 241 and valve 201 from a pressure controller (not shown). Valve 201 is then closed and valve 211 is opened to allow the carrier gas to pressurize precursor reservoir 11 to pressure $P_{tot}$. This dose is delivered by opening valve 231. Carrier gas from tube 91 promotes transport of the metered dose to the deposition chamber.

In an isothermal deposition zone, material is generally deposited on all surfaces exposed to the precursor vapors, including substrates and the interior chamber walls. Thus it is appropriate to report the precursor doses used in terms of moles per unit area of the substrates and exposed chamber walls.

The liquids and solutions described herein may also be used as metal-containing precursors for other types of deposition processes, such as spray coating, spin coating or sol-gel formation of mixed metal oxides. The high solubility and miscibility of these precursors is an advantage in forming the required solutions.

The amides disclosed in these examples appeared to be non-pyrophoric by the methods published by the United States Department of Transportation. One test calls for placing about 5 milliliters of the material on an non-flammable porous solid, and observing that no spontaneous combustion occurs. Another test involves dropping 0.5 milliliters of the liquid or solution on a Whatman No. 3 filter paper, and observing that no flame or charring of the paper occurs.

The precursors generally react with moisture in the ambient air, and should be stored under an inert, dry atmosphere such as pure nitrogen gas.

The invention may be understood with reference to the following examples which are for the purpose of illustration only and which are not limiting of the invention, the full scope of which is set forth in the claims which follow.

EXAMPLE 1

CVD of Zirconium Silicate

A solution (1% by weight) of tris(tert-butoxy)silanol in mesitylene was pumped at a rate of 6 ml/hour into a $\frac{1}{16}$" O.D. tee joint through which nitrogen gas flowed at 0.4 L/min. The resulting fog flowed into a tube heated to 250° C. A solution (1% by weight) of tetrakis(ethylmethylamido) zirconium in mesitylene was pumped at a rate of 12 ml/hour into another tee joint through which nitrogen gas flowed at 0.4 L/min. The resulting fog flowed into the same heated tube. The gas pressure was maintained at 5 Torr by a vacuum pump attached to the outlet of the glass tube by a liquid nitrogen trap. Substrates of silicon and glassy carbon placed inside the tube were coated with a film of zirconium silicate whose thickness varied along the length of the tube. Analysis of the film by Rutherford backscattering spectroscopy gave a composition $ZrSi_2O_6$ for films deposited on glassy carbon. No carbon or nitrogen was detected in the film. The refractive indexes of films deposited on silicon were found to be about 1.6 by ellipsometry.

EXAMPLE 2

ALD of Zirconium Silicate

Example 1 was repeated except that the precursors were injected in alternate pulses spaced 5 seconds apart, instead of continuously. A film of similar composition, $ZrSi_2O_6$, was deposited with uniform thickness along the whole length of the heated zone. The thickness was about 0.3 nm per cycle.

EXAMPLE 3

CVD of Hafnium Silicate

Example 1 was repeated with tetrakis(ethylmethylamido) hafnium in place of tetrakis(ethylmethylamido)zirconium. Films of composition approximately $HfSi_2O_6$ were formed. No carbon or nitrogen was detected in the film. The refractive indexes of films deposited on silicon were found to be about 1.6 by ellipsometry.

EXAMPLE 4

ALD of Hafnium Silicate

Example 3 was repeated except that the precursors were injected in alternate pulses spaced 5 seconds apart, instead of continuously. A film of similar composition, $HfSi_2O_6$, was deposited with uniform thickness along the whole length of the heated zone. The thickness was about 0.3 nm per cycle.

EXAMPLE 5

CVD of Yttrium Silicate

Example 1 was repeated with tris(tert-butyl (trimethylsilyl)amido)yttrium in place of tetrakis (ethylmethylamido)zirconium. Films of composition approximately $Y_2Si_2O_7$ were formed. No carbon or nitrogen was detected in the film. The refractive indexes of films deposited on silicon were found to be about 1.6 by ellipsometry.

EXAMPLE 6

ALD of Yttrium Silicate

Example 5 was repeated except that the precursors were injected in alternate pulses spaced 5 seconds apart, instead of continuously. A film of similar composition, $Y_2Si_2O_7$, was deposited with uniform thickness along the whole length of the heated zone. The thickness was about 0.3 nm per cycle. Composition approximately $Y_2Si_2O_7$.

EXAMPLE 7

CVD of Lanthanum Silicate

Example 1 was repeated with tris(bis(trimethylsilyl)amido)lanthanum in place of tetrakis(ethylmethylamido)zirconium and tetradecane in place of mesitylene. Films with a La:Si ratio of about 0.9 were formed on a glassy carbon substrate at a substrate temperature of 250° C. No carbon or nitrogen was detected in the films.

EXAMPLE 8

ALD of Lanthanum Silicate

Example 7 was repeated except that the precursors were injected in alternate pulses spaced 5 seconds apart, instead of continuously. A film of similar composition was deposited with uniform thickness along the whole length of the heated zone.

EXAMPLE 9

CVD of Lithium Phosphate

Liquid lithium bis(ethyldimethylsilyl)amide (1 part by weight) was mixed with mesitylene (99 parts). The resulting solution was nebulized by pumping at a rate of 12 ml/hour into a tee joint into nitrogen gas flowing at 0.30 L/min into the deposition zone inside a tube (24 mm inside diameter) in a furnace heated to 250° C. Simultaneously a 1% mesitylene solution of diisopropylphosphate was similarly nebulized into another nitrogen carrier gas stream flowing at 0.30 L/min into the same tube furnace. The gas pressure was maintained at 5 Torr by a vacuum pump attached to the outlet of the glass tube by a liquid nitrogen trap. A thin film was deposited on a silicon substrate placed on the bottom of the glass tube, as well as on the inside of the tube. The thickness profile showed a peak near the gas entrance to the tube furnace. The film was analyzed by X-ray photoelectron spectroscopy to contain lithium, phosphorus and oxygen.

EXAMPLE 10

ALD of Lithium Phosphate

Example 9 was repeated with the change that the materials were introduced in alternating pulses spaced 5 seconds apart in time. A similar lithium phosphate film was deposited, except that the thickness was nearly constant throughout the deposition zone.

COMPARATIVE EXAMPLE 1

Control Deposition with Only tris(tert-butoxy)silanol

Example 1 was repeated using only the silicon precursor and no zirconium precursor. No film was deposited.

COMPARATIVE EXAMPLE 2

Control Deposition with Only tetrakis(ethylmethylamido)zirconium

Example 1 was repeated using only the zirconium precursor and no silicon precursor. No film was deposited.

COMPARATIVE EXAMPLE 3

Control Deposition with Only tetrakis(ethylmethylamido)hafnium

Example 3 was repeated using only the hafnium precursor and no silicon precursor. No film was deposited.

COMPARATIVE EXAMPLE 4

Control Deposition with Only tris(tert-butyl(trimethylsilyl)amido)yttrium

Example 5 was repeated using only the yttrium precursor and no silicon precursor. No film was deposited.

COMPARATIVE EXAMPLE 5

Control Deposition with Only tris(bis(trimethylsilyl)amido)lanthanum

Example 7 was repeated using only the lanthanum precursor and no silicon precursor. No film was deposited.

COMPARATIVE EXAMPLE 6

Control Deposition with Only Diisopropylphosphate

Example 9 was repeated using only the phosphorus precursor and no lithium precursor. No film was deposited.

COMPARATIVE EXAMPLE 7

Control Deposition with Only Lithium bis(ethyldimethylsilyl)amide

Example 9 was repeated using only the lithium precursor and no phosphorus precursor. No film was deposited.

EXAMPLE 11

ADL Formation of Metal Silicates and Phosphates

The ALD examples 2, 4, 6, 8 and 10 were repeated using automobile fuel injectors (Ford model CM-4722 F13Z-9F593-A) to deliver pulses of the solutions of precursors into the nitrogen carrier gas. About 0.05 m of solution was delivered each time that a valve was opened for about 50 milliseconds. Similar results were obtained.

The ALD examples 2, 4, 6, 8 and 10 were repeated using a 6-port sampling valves (Valco model EP4C6WEPH, Valco Instruments, Houston, Tex.) normally used for injecting samples into gas chromatographs to deliver pulses of tetradecane solutions into the nitrogen carrier gas. External sample loops having volumes of 50 microliters were used. Each time that a valve was opened, about 50 microliters of solution flowed into a $\frac{1}{16}$" O.D., 0.040" I.D. nickel tube in which the solution was vaporized by heat from hot oil flowing over the outside of the tube. Nitrogen carrier gas moved the vapor from the small tube into the ALD reactor tube. Similar results were obtained.

In another series of examples, pulses of those precursors that are liquids at room temperature were delivered for ALD experiments similar to examples 2, 4, 6, 8 and 10 using 4-port sampling valves with small (0.5 microliter) internal sampling loops (Valco model EH2CI4WE.5PH, Valco Instruments, Houston, Tex.). Each time that a valve was opened, about 0.5 microliters of liquid flowed into a $\frac{1}{16}$" O.D., 0.040" I.D. nickel tube in which the liquid was vaporized by heat from hot oil flowing over the outside of the tube. Nitrogen carrier gas moved the vapor from the small tube into the ALD reactor tube. Similar results were obtained.

EXAMPLE 12

ALD of Hafnium Oxide

A hafnium oxide layer was deposited using the apparatus of FIG. 1. Doses of $0.5 \times 10^{-9}$ moles/cm$^2$ of tetrakis (dimethylamido)hafnium vapor and $4 \times 10^{-9}$ moles/cm$^2$ of water vapor were injected alternately every 5 seconds into a deposition chamber held at 250° C. The chamber was also fed a continuous flow of nitrogen carrier gas sufficient to maintain a pressure of 0.15 Torr. The deposition chamber had a cross-sectional area of 2.3 square centimeters in the plane perpendicular to the direction of gas flow through the chamber. The outlet of the deposition chamber was attached to a vacuum pump with capacity (195 liters/minute) sufficient to pump a volume equal to the deposition chamber in about 0.012 seconds.

As a result of these reaction conditions, a transparent, electrically insulating hafnium oxide film was deposited on substrates in the deposition chamber and onto its inner walls. Its composition was determined to be $HfO_2$ by Rutherford backscattering spectroscopy (RBS) of a film on a glassy carbon substrate. No carbon or nitrogen was detected (<1 atomic percent). By ellipsometry, its thickness was determined to be 0.1 nanometer/cycle and its refractive index 2.05. Combining data from RBS and ellipsometry yielded a density of about 9. The thickness was constant over the whole deposition region, to within the estimated measurement error of about 1%. Small-angle X-ray reflectivity measurements confirmed the thickness and gave a density of 9.23 g/cm$^3$. X-ray reflectivity also showed that the films are very smooth, with root mean square surface roughness about 0.4 nm for a film 43 nm thick. Scanning electron microscopy showed that films grown at 150° C. are even smoother than the ones grown at 250° C.

Figure 3:
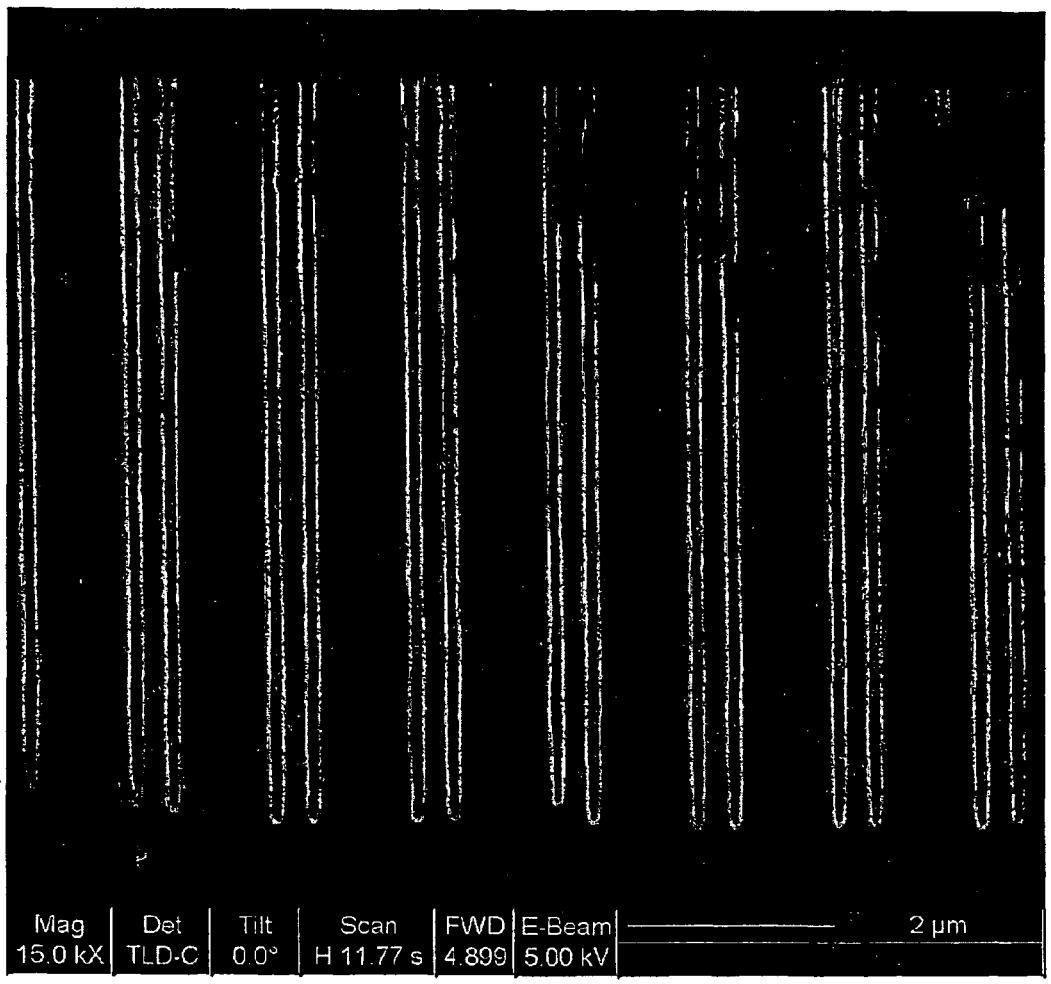
FIG. 3 is a cross-sectional scanning electron micrograph of holes in a silicon wafer uniformly coated with hafnium dioxide using one embodiment of the invention.

Repeating Example 12 with higher doses of either reactant did not increase the film thickness or change its properties. These results show that the surface reactions are self-limiting. This conclusion was confirmed by placing inside the deposition chamber 110 a quartz crystal microbalance (not shown), which showed that the amount of mass deposited first increased and then reached a plateau as the size of each dose was increased. As a result of these self-limiting surface reactions, uniform films could be deposited inside holes with ratios of length to diameter over 50. Uniformity of thickness inside these holes was improved by increasing the dose to 10 times the minimum required for saturation of the reactions on a flat surface without the holes. Reducing the capacity (speed) of the vacuum pump also helps to improve the step coverage by reducing the linear velocity of the vapors through the deposition chamber, thereby increasing the time during which the vapors can diffuse down the holes, i.e. increasing the flux (Langmuirs of exposure). FIG. 3 shows a scanning micrograph of holes coated with hafnium oxide, cleaved to reveal their highly uniform thickness. The hafnium oxide layer is the bright line outlining each of the narrow vertical holes in the silicon, which appears as a dark background. At the top of the micrograph is the upper surface of the silicon from which the holes were etched prior to the deposition of the hafnium oxide.

Repeating Example 12 with substrate temperatures in the range from 100° C. to 300° C. gave similar results. At temperatures above 300° C., the thickness increased with increasing the dose of tetrakis(dimethylamido)hafnium. This shows that the surface reaction is not self-limiting at temperatures above 300° C., due to thermal decomposition of tetrakis(dimethylamido)hafnium.

EXAMPLE 13

ALD of Zirconium Oxide

Example 12 was repeated with tetrakis(dimethylamido)zirconium in place of tetrakis(dimethylamido)hafnium. Films of zirconium dioxide with similar properties were deposited.

EXAMPLE 14

ALD of Hafnium Oxide

Example 12 was repeated with tert-butanol vapor in place of water vapor. Films of hafnium dioxide with similar properties were deposited.

EXAMPLE 15

ALD of Tantalum Oxide

Example 12 was repeated with ethylimidotris (diethylamido)tantalum vapor in place of tetrakis (dimethylamido)hafnium vapor. Transparent films of $Ta_2O_5$ were deposited. They have a refractive index of 2.2, and a thickness of about 0.06 nm per cycle.

EXAMPLE 16

ALD of Aluminum Phosphate

ALD was carried out using alternating doses of $3 \times 10^{-9}$ moles/cm$^2$ of the vapors of trimethylaluminum and diisopropylphosphate at a substrate temperature of 400° C. Transparent aluminum phosphate films with approximate composition $Al_2P_4O_{13}$ were deposited at a rate of 0.1 nm per cycle. They had a refractive index of about 1.5.

EXAMPLE 17

ALD of Aluminum Silicate

ALD was carried out using alternating doses of $3 \times 10^{-9}$ moles/cm$^2$ of trimethylaluminum vapor and $1.2 \times 10^{-8}$ moles/cm$^2$ of tris(tert-butoxy)silanol vapor at a substrate temperature of 300° C. Transparent aluminum silicate films with approximate composition $Al_2Si_8O_{19}$ were deposited at a remarkably high rate of 1 nm per cycle. They had a refractive index of about 1.48. The surfaces of the films are very smooth; atomic force microscopy determined a root mean square roughness of less than 0.8 nm for an aluminum silicate film 150 nm thick. The tensile stress in a film 2 micrometers thick on a silica substrate was measured to be about 0.2 giga-Pascals. A similar film deposited on single-crystalline silicon showed a smaller tensile stress of 0.03 giga-Pascals. A film 6 microns thick showed cracks and delamination because of the tensile stress.

This tensile stress can be reduced, eliminated, or even reversed to compressive stress by plasma treatment. The deposition is temporarily halted after a thin layer (such as 5 to 10 nm) has been deposited, a radio-frequency plasma (in a low-pressure gas such as $O_2$+argon) is applied, and then the plasma power is stopped and the deposition is resumed. Multiple cycles of deposition and plasma treatment may be used to build up thicker layers with tensile or compressive stress values adjusted to the requirements of particular applications, particularly those requiring thicker films.

EXAMPLE 18

ALD of Aluminum Silicate

ALD was carried out using alternating doses of $3 \times 10^{-9}$ moles/cm$^2$ of trimethylaluminum vapor and $3 \times 10^{-8}$ moles/cm$^2$ of tris(tert-butoxy)silanol vapor at a substrate temperature 200° C. Transparent aluminum silicate films with approximate composition $Al_2Si_{16}O_{35}$ were deposited at a remarkably high rate of 2 nm per cycle. They had a refractive index of about 1.47.

EXAMPLE 19

ALD of Aluminum Silicate

ALD was carried out with alternating doses of $3\times10^{-9}$ moles/cm$^2$ of tris(dimethylamino)aluminum vapor and $3\times10^{-8}$ moles/cm$^2$ of tris(tert-butoxy)silanol vapor at a substrate temperature 250° C. An aluminum silicate film was formed with thickness 0.1 nm/cycle and a refractive index of about 1.46.

EXAMPLE 20

ALD of Aluminum Silicate

Example 19 was repeated with tris(tert-pentyloxy)silanol vapor in place of the tris(tert-butoxy)silanol vapor. Similar results were obtained

EXAMPLE 21

ALD of Aluminum Silicate

Example 19 was repeated with a dose of water vapor between the doses of tris(dimethylamino)aluminum vapor and tris(tert-butoxy)silanol vapor. A similar film was obtained with very uniform thickness of 0.1 nm/cycle (±1%) along the direction of gas flow.

EXAMPLE 22

ALD of Lanthanum Silicate

Example 12 was repeated with tris(bis(trimethylsilyl)amido)lanthanum vapor in place of tetrakis(dimethylamido)hafnium vapor and with the apparatus of FIG. 2, used as described herein above. Transparent oxide films with a La:Si ratio of about 2 were formed on substrates at a substrate temperature of 250° C. No carbon or nitrogen was detected in the films. They have a refractive index of 1.7, and a thickness of about 0.1 nm per cycle.

EXAMPLE 23

ALD of Lanthanum Oxide

Figure 2:
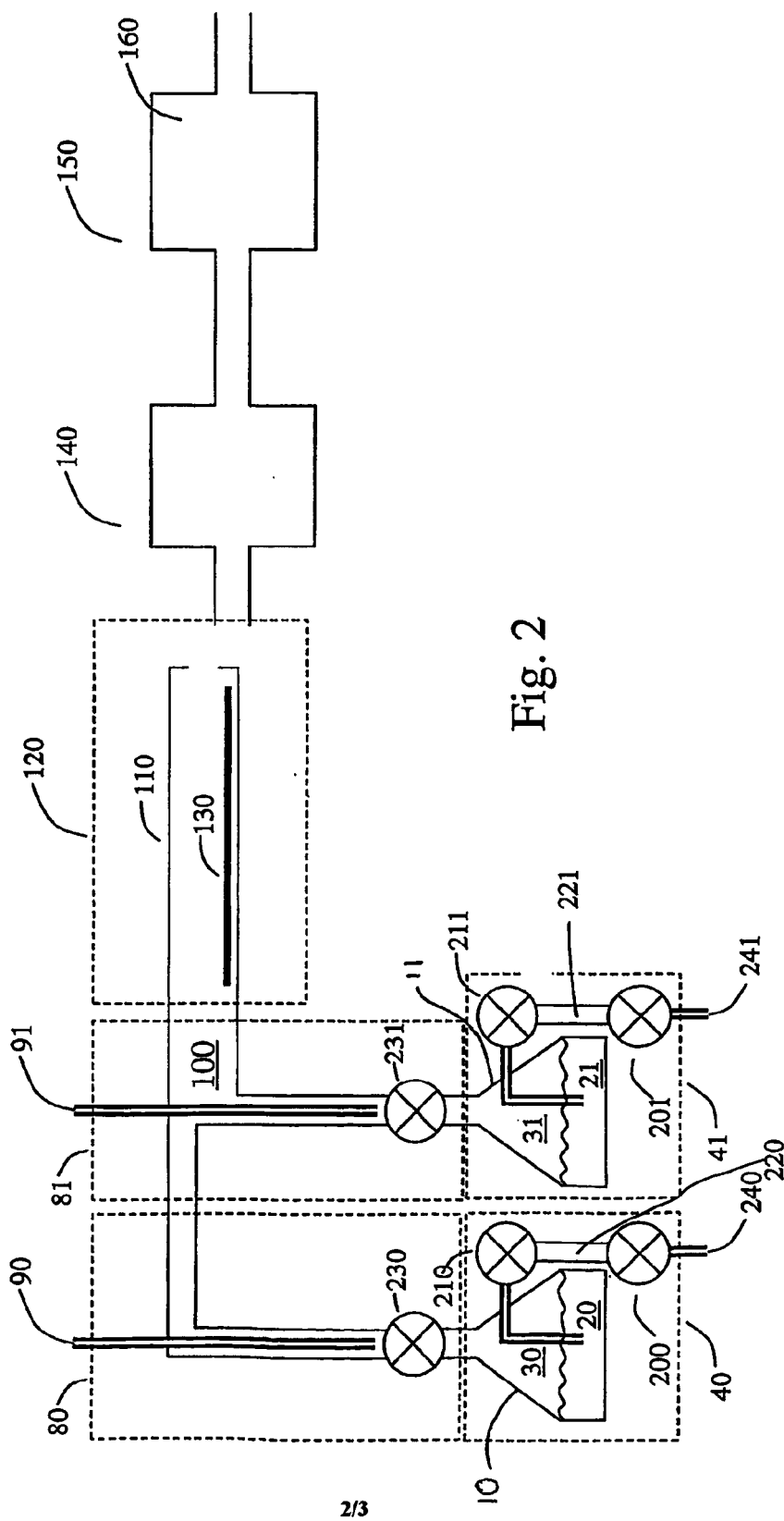
FIG. 2 is a cross-sectional illustration of an atomic deposition layer apparatus used in the practice of at least one embodiment of the invention.

ALD can be carried out with alternating doses of tris(2,2,6,6-tetramethylpiperidido)lanthanum vapor using the apparatus of FIG. 2 and water vapor to form lanthanum oxide films.

EXAMPLE 24

ALD of Silicon Dioxide

ALD can be carried out with alternating doses of tetraisocyanatosilane vapor and tris(tert-butoxy)silanol vapor to form silicon dioxide films. Larger fluxes of exposure ($>10^{-7}$ Langmuirs) are required for these less reactive precursors.

Those skilled in the art will recognize or be able to ascertain using no more than routine experimentation, many equivalents to the specific embodiments of the invention described specifically herein. Such equivalents are intended to be encompassed in the scope of the following claims.

What is claimed is:

1. A process for forming materials comprising silicon, oxygen and one or more metals or metalloids, comprising:
    reacting the vapor of one of an alkoxysilanol and an alkoxysilanediol together with a vapor of one or more of a metal compound and a metalloid compound.

2. A process for forming materials comprising silicon, oxygen and one or more metals or metalloids, comprising:
    exposing a substrate alternately to the vapor of one or an alkoxysilanol and an alkoxysilanediol and the vapor of one or more of a metal compound or a metalloid compound to form a film on the substrate.

3. The process of claim 1, wherein compound is deposited as a film on a substrate.

4. The process as in claim 1 or 2, wherein the silanol has the formula

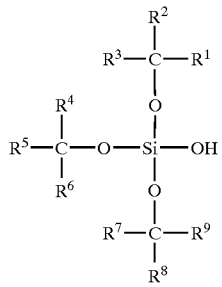

where the R″ represents hydrogen, alkyl groups, fluoroalkyl groups or alkyl groups substituted by other atoms or groups, R″ being any one of the groups R$^1$ through R$^9$, and where R″ are the same or different.

5. The process of claim 4, wherein the groups R″ contain between one and four carbons and are the same or different.

6. The process of claim 5, wherein the groups R″ are all methyl groups.

7. The process of claim 5, wherein R$^1$, R$^4$ and R$^7$ are ethyl groups and R$^2$, R$^3$, R$^5$, R$^6$, R$^8$ and R$^9$ are methyl groups and the silanol has the formula

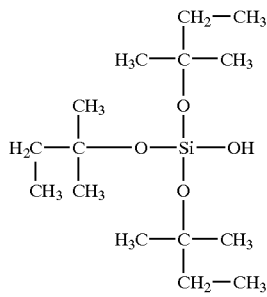

8. The process of claim 1 or 2, wherein a metal or metalloid compound contains metal-nitrogen or metalloid-nitrogen bonds.

9. The process of claim 8, wherein a metal or metalloid compound is selected from Table 1.

10. The process of claim 1 or 2, wherein a metal compound is selected from Table 2.

11. The process of claim 1 or 2, wherein a metal or metalloid compound is selected from Table 3.

12. A process for forming materials comprising phosphorus, oxygen and one or more metals or metalloids, comprising:
    reacting a vapor of a bis(alkyl)phosphate with a vapor of one or more of a metal compound and a metalloid compound.

13. A process for forming materials comprising phosphorus, oxygen and one or more metals or metalloids, comprising:
    exposing a substrate alternately to a vapor of a bis(alkyl) phosphate and a vapor of one or more of a metal compound and metalloid compound to form a film on the substrate.

14. The process of claim 12, wherein the material comprising phosphorus, oxygen and one or more metals or metalloids is deposited as a film on a substrate.

15. The process as in claim 12 or 13, wherein the bis(alkyl)phosphate has the formula

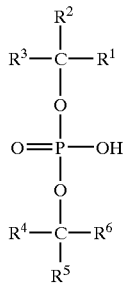

where the R″ represents hydrogen, alkyl groups, fluoroalkyl groups or alkyl groups substituted by other atoms or groups, R″ being any one of the groups $R^1$ through $R^6$, and wherein R″ are the same or different.

16. The process of claim 15, wherein the groups R″ contain between one and four carbons and may be the same or different.

17. The process of claim 16, wherein the groups $R^1$, $R^3$, $R^4$ and $R^6$ are methyl groups, the groups $R^2$ and $R^5$ are hydrogen, and the compound has the formula

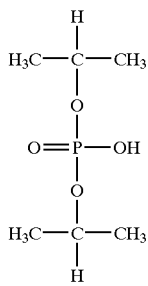

18. The process of claim 12 or 13, wherein a metal or metalloid compound contains metal-nitrogen or metalloid-nitrogen bonds.

19. The process of claim 18, wherein a metal or metalloid compound is chosen from Table 1.

20. The process of claim 12 or 13, wherein a metal compound is chosen from Table 2.

21. The process of claim 13 or 14, wherein a metal or metalloid compound is selected from Table 3.

22. A process for forming a material comprising a metal and oxygen, comprising:
    exposing a substrate to a vapor of one or more arene hydrates and a vapor of one or more metal compounds to form a metal oxide.

23. The process of claim 22, wherein the arene hydrate is benzene hydrate, a naphthalene hydrate, a substituted benzene hydrate or a substituted naphthalene hydrate.

24. A process for forming a metal oxide, comprising:
    exposing a heated surface alternately to the vapor of one or more metal amides having an amido group selected from the group consisting of dialkylamido, disilylamido and (alkyl)(silyl) amido moieties, and then to the vapors of water or an alcohol.

25. A process as in claim 24, wherein the alcohol is an arene hydrate.

26. A process as in claim 24, wherein the metal amide or amides are chosen from Table 1.

27. A process for forming material comprising oxygen and one or more metals, comprising:
    exposing a surface alternately to the vapor of one or more organometallic compounds and then to the vapors of an arene hydrate.

28. A process as in claim 27, wherein the organometallic compounds are chosen from Table 2.

29. A process as in claim 24, in which a metal amide compound is a liquid at room temperature.

30. A process as in claim 29, in which the liquid dialkylamido metal compound is tetrakis(ethylmethylamido) hafnium, $Hf(NetMe)_4$.

31. A process as in any one of claims 24, 26, 29 or 30, in which the metal oxide film covers an aspect ratio over 40.

* * * * *